US008512751B2

(12) United States Patent
Rariy et al.

(10) Patent No.: US 8,512,751 B2
(45) Date of Patent: Aug. 20, 2013

(54) PHARMACEUTICAL COMPOSITIONS FOR SLEEP DISORDERS

(75) Inventors: Roman V. Rariy, Allston, MA (US); Michael Heffernan, Hingham, MA (US)

(73) Assignee: Collegium Pharmaceutical, Inc., Cumberland, RI (US)

( * ) Notice: Subject to any disclaimer, the term of this patent is extended or adjusted under 35 U.S.C. 154(b) by 1278 days.

(21) Appl. No.: 11/793,392

(22) PCT Filed: Dec. 20, 2005

(86) PCT No.: PCT/US2005/046049
§ 371 (c)(1),
(2), (4) Date: Jun. 19, 2007

(87) PCT Pub. No.: WO2006/069030
PCT Pub. Date: Jun. 29, 2006

(65) Prior Publication Data
US 2008/0200508 A1    Aug. 21, 2008

Related U.S. Application Data

(60) Provisional application No. 60/637,655, filed on Dec. 20, 2004.

(51) Int. Cl.
*A61K 31/4164* (2006.01)
(52) U.S. Cl.
USPC .......................................... 424/488; 514/385
(58) Field of Classification Search
None
See application file for complete search history.

(56) References Cited

U.S. PATENT DOCUMENTS

| 5,075,290 | A | 12/1991 | Findley et al. |
| 5,082,665 | A | 1/1992 | Verny |
| 5,166,158 | A | 11/1992 | Zimmerman et al. |
| 5,356,934 | A | 10/1994 | Robertson et al. |
| 5,612,379 | A | 3/1997 | Laurent |
| 6,030,992 | A | 2/2000 | Gitter et al. |
| 6,143,792 | A | 11/2000 | Cattelin |
| 6,210,712 | B1 * | 4/2001 | Edgren et al. ............ 424/473 |
| 6,221,396 | B1 | 4/2001 | Chao et al. |
| 6,303,595 | B1 | 10/2001 | Andrews |
| 6,331,536 | B1 | 12/2001 | Radulovacki et al. |
| 6,548,082 | B1 | 4/2003 | Rubin et al. |
| 6,599,529 | B1 * | 7/2003 | Skinhoj et al. ........... 424/458 |
| 6,649,183 | B2 | 11/2003 | Rubin et al. |
| 6,727,242 | B2 | 4/2004 | Radulovacki et al. |
| 6,986,901 | B2 | 1/2006 | Meisel et al. |
| 7,160,898 | B2 | 1/2007 | Radulovacki et al. |
| 2002/0051815 | A1 * | 5/2002 | Rubin et al. .............. 424/452 |
| 2003/0091632 | A1 * | 5/2003 | Campbell et al. .......... 424/468 |
| 2003/0130266 | A1 | 7/2003 | Radulovacki et al. |
| 2006/0039866 | A1 | 2/2006 | Rao et al. |
| 2006/0039867 | A1 | 2/2006 | Rao et al. |

FOREIGN PATENT DOCUMENTS

| CA | 2321900 A1 | 9/1999 |
| CA | 2371822 A1 | 9/2000 |
| CN | 1530104 A | 9/2004 |
| EP | 0 442 423 A1 | 8/1991 |
| EP | 0 442 424 A1 | 8/1991 |
| EP | 0 518 767 A2 | 12/1992 |
| EP | 1 230 921 A1 | 8/2002 |
| JP | 2002-538102 A | 11/2002 |
| JP | 2003-503341 A | 1/2003 |
| WO | WO 99/00119 A1 | 1/1999 |
| WO | WO 99/25356 A1 | 5/1999 |
| WO | WO 99/43319 A1 | 9/1999 |
| WO | WO 99/65490 A2 | 12/1999 |
| WO | WO 99/65571 A2 | 12/1999 |
| WO | WO-00/30648 A1 | 6/2000 |
| WO | WO-00/51582 A2 | 9/2000 |
| WO | WO 00/51582 A2 | 9/2000 |
| WO | WO-01/00182 A1 | 1/2001 |
| WO | WO-01/93844 A2 | 12/2001 |
| WO | WO 02/36113 A1 | 5/2002 |
| WO | WO 2004/041272 A2 | 5/2004 |
| WO | WO-2004/089288 A2 | 10/2004 |
| WO | WO 2006/069030 A1 | 6/2006 |

OTHER PUBLICATIONS

English translation of a first Office Action regarding Chinese Patent Application No. 200580043729.6, issued Jul. 5, 2009.
English translation of a second Office Action for Chinese Patent Application No. 200580043729.6, issued Apr. 30, 2010.
Hsyu et al., Pharmaceutical Research. 11(1):156-159, (1994).
Extended European Search Report in corresponding European Patent Application No. EP 05854713, dated Aug. 28, 2012.
Armstrong, D.J., et al., "MDL 72222 (a 5-HT antagonist) Antagonizes the Pulmonary Depressor and Respiratory Chemoreflexes Evoked by Phenylbiguanide in Anaesthetized Rabbits," *J. Physiol.*, vol. 365, 104P, 1985.
Badr, M. Safwan, et al., "Treatment of Refractory Sleep Apnea with Supplemental Carbon Dioxide," *Am J Respir Crit Care Med*, vol. 150, pp. 561-564,1994.
Benington, Joel H., et al., "Methodology: Scoring and Computerized Methods: Scoring Transitions to REM Sleep in Rats Based on the EEG Phenomena of Pre-REM Sleep: An improved Analysis of Sleep Structure," *Sleep*, vol. 17, No. 1, pp. 28-36, 1994.
Bisgard, G.E., et al., "Effects of Dopamine, Norepinephrine and 5-Hydroxytryptamine on the Carotid Body of the Dog," *Respiration Physiology*, vol. 37, pp. 61-80, 1979.

(Continued)

*Primary Examiner* — Robert A Wax
*Assistant Examiner* — Randeep Singh
(74) *Attorney, Agent, or Firm* — Marshall, Gerstein & Borun LLP

(57) ABSTRACT

Pharmaceutical compositions are provided for the pharmacological treatment of breathing disorders and, more specifically, to compositions containing agents having serotonin receptor modulating activity for the alleviation of sleep apnea (central and obstructive) and other sleep-related breathing disorders wherein the active ingredients are released such as to extend effective blood plasma concentrations across the period of sleep.

31 Claims, 4 Drawing Sheets

(56) References Cited

OTHER PUBLICATIONS

Black, Andrew M.S., et al., "Species difference in carotid body response of cat and dog to dopamine and serotonin," *American Journal of Physiology*, vol. 223, No. 5, pp. 1097-1102, 1972.
Butler, A. et al., "Pharmacological properties of GR38032F, a novel antagonist at 5-$HT_3$ receptors," *Br. J. Pharmacol.*, vol. 94, pp. 397-412, 1988.
Carley, D. W., et al., "Sleep Apnea in Normal and REM Sleep-Deprived Normotensive Wistar-Kyoto and Spontaneously Hypertensive (SHR) Rats," *Physiology & Behavior*, vol. 59, Nos. 4/5, pp. 827-831, 1996.
Carley, David W., et al., "The Heart and Sleep: Hydralazine Reduces Elevated Sleep Apnea Index in Spontaneously Hypertensive (SHR) Rats to Equivalence With Normotensive Wistar-Kyoto Rats," *Sleep*, vol. 19, No. 5, pp. 363-366, 1996.
Christon, James, et al., "Effects of inspired gas on sleep-related apnea in the rat," *J. Appl. Physiol.*, vol. 80, pp. 2102-2107, 1996.
Coon, R. L., "Reflex effects of lung inflation on tracheomotor tone observed during apnea produced by the Hering-Breuer reflex," *J. Appl. Physiol.*, vol. 76, pp. 2546-2551, 1994.
De Boer, Th., "The Pharmacologic Profile of Mirtazapine," *J. Clin Psychiatry*, vol. 57 (suppl. 4), pp. 19-25, 1996.
Devane, C. Lindsay, "Differential Pharmacology of Newer Antidepressants," *J. Clin Psychiatry*, vol. 59 (suppl 20), pp. 85-93, 1998.
Douglas, Neil J., et al., "Effects of CPAP on Vigilance and Related Functions in Patients with the Sleep Apnea/Hypopnea Syndrome," *Sleep*, vol. 23, Suppl. 4, pp. S147-S149, 2000.
Downs, Daniel H. et al., "The Effect of Antihistamines on the Laryngeal Chemoreflex," *Laryngoscope*, vol. 105, pp. 857-861, 1995.
Friend, David R., et al., "Mathematical Modeling of a Novel Controlled-Release Dosage Form," *Drug Delivery Technology*, vol. 1, No. 1, 2001.
Goda, Y., et al. "The role of 5-$HT_3$ receptor-medicated mechanisms on 5-HT-induced apnea in anesthetized rats," *European J. Phramacology*, vol. 183, No. 3, pp. 705-706, 1990.
Greulich, W., et al., "Schlafverhalten bei Patienten mit Morbus Parkinson: Sleep Behaviour in Patients with Parkinson's Disease," *Somnologie*, vol. 2, pp. 163-171, 1998.
Grogaard, Jens, et al., "Effect of Beta-Adrenergic Agonists on Apnea Reflexes in Newborn Lambs," *Pediatr. Res.*, vol. 17, pp. 213-219, 1983.
Hagan, Russell M., et al., "Effect of the 5-$HT_3$ receptor antagonist, GR38032F, on responses to injection of a neurokinin agonist into the ventral tegmental area of the rat brain," *European Journal of Pharmacology*, vol. 138, pp. 303-305, 1987.
Hanzel, Douglas A., et al., "Response of Obstructive Sleep Apnea to Fluoxetine and Protriptyline," *Chest*, vol. 100, No. 2, pp. 416-421, 1991.
Harding, Susan M., "Sleep in Fibromyalgia Patients: Subjective and Objective Findings," *The American Journal of the Medical Sciences*, vol. 315, No. 6, pp. 367-376, 1998.
Hilaire, Gérard, et al., "Changes in Serotonin Metabolism May Elicit Obstructive Apnoea in the Newborn Rat," *Journal of Physiology*, vol. 466, pp. 367-382, 1993.
Hudgel, David W., "Pharmacologic treatment of obstructive sleep apnea," *J. Lab Clin Med*, vol. 126, No. 1, pp. 13-18, Jul. 1995.
Hudgel, David W., et al., "Abnormal Serotonergic Stimulation of Cortisol Production in Obstructive Sleep Apnea," *American Journal of Respiratory and Critical Care Medicine*, vol. 152, pp. 186-192, 1995.
Hudgel, David W., et al., "Mechanics of the respiratory system and breathing pattern during sleep in normal humans," *J. Appl. Physiol.*, vol. 56, pp. 133-137, 1984.
Jacobs, Louise, et al. "Reflex Apnea, Bradycardia, and Hypotension Produced by Serotonin and Phenyldiguanide Acting on the Nodose Ganglia of the Cat," *Circulation Research*, vol. 29, pp. 145-155, 1971.
Kopelman, P. G., et al., "Short term use of fluoxetine in asymptomatic obese subjects with sleep-related hypoventilation," *International Journal of Obesity*, vol. 16, pp. 825-830, 1992.

Kraiczi, Holger et al., "Effect of Serotonin Uptake Inhibition on Breathing during Sleep and Daytime Symptoms in Obstructive Sleep Apnea," *Sleep*, vol. 22, No. 1, pp. 61-67, 1999.
Kubin, L., et al., "Serotonergic excitatory drive to hypoglossal motoneurons in the decerebrate cat," *Neuroscience Letters*, vol. 139, pp. 243-248, 1992.
Mancia, Giuseppe, et al., "Cardiovascular Regulation during Sleep," *Physiology in Sleep*, Academic Press, Inc., New York, NY, pp. 1-55, 1980.
Matsumoto, S., "Effects of Carotid Body Chemoreceptor Stimulation by 5-HT on Phrenic Nerve Activity and Ventilation in the Rabbit," *Arch. Int. Pharmacodyn*, vol. 254, pp. 282-292, 1981.
Mcqueen, D. S., et al., "Activation of P2X receptors for adenosine triphosphate evokes cardiorespiratory reflexes in anaesthetized rats," *Journal of Physiology*, No. 507.3, pp. 843-855, 1998.
Mendelson, Wallace B., et al., "Buspirone Administration to Sleep Apnea Patients," *J. Clin. Psychopharmacol*, vol. 11, No. 1, pp. 71-72, 1991.
Mendelson, Wallace B., et al., "Effects of Buspirone on Sleep and Respiration," *Am Rev Respir Dis*, vol. 141, pp. 1527-1530, 1990.
Mendelson, Wallace B., et al., "Periodic Cessation of Respiratory Effort During Sleep in Adult Rats," *Physiology & Behavior*, vol. 43, pp. 229-234, 1988.
Monti, Daniel, et al, "p-SPA, a Peripheral Adenosine $A_1$ Analogue, Reduces Sleep Apneas in Rats," *Pharmacology Biochemistry and Behavior*, vol. 53, No. 2, pp. 341-345, 1996.
Monti, Daniel, et al., "Adenosine Analogues Modulate the Incidence of Sleep Apneas in Rats," *Pharmacology Biochemistry and Behavior*, vol. 51, No. 1, pp. 125-131, 1995.
Morin, Didier, "Compared effects of serotonin on the inspiratory activity of glossopharyngeal, vagal, hypoglossal and cervical motoneurons in neonatal rat brain stem-spinal cord preparations," *Neuroscience Letters*, vol. 160, pp. 61-64, 1993.
Orem, John, et al., "Breathing During Sleep and Wakefulness in the Cat," *Respiration Physiology*, vol. 30, pp. 265-289, 1977.
Petkov, V. D., et al., "Effects of Agonists and Antagonists of Some Serotonin-Receptor Subtypes on Memory and Their Modulation by the 5-HT-Uptake Inhibitor Fluoxetine," *ACTA Physiologica & Pharmacologica Bulgarica*, vol. 20, pp. 83-90, 1994.
Phillipson, Eliot A., "Respiratory Adaptations in Sleep," *Ann. Rev. Physiol.*, vol. 40, pp. 133-156, 1978.
Planés, Carole, et al., "Effect of Celiprolol Treatment in Hypertensive Patients with Sleep Apnea," *Sleep*, vol. 22, No. 4, pp. 507-513, 1999.
Ponsonby, A-L, et al., "Factors related to infant apnoea and cyanosis: A population-based study," *J. Paediatr. Child Health*, vol. 33, pp. 317-323, 1997.
Puzantian, Talia, "Mirtazapine, an antidepressant," *Am J Health-Syst Pharm*, vol. 55, pp. 44-49, 1998.
Radulovacki, M., et al., "Adenosine Analogs and Sleep in Rats," *The Journal of Pharmacology and Experimental Therapeutics*, vol. 228, No. 2, pp. 268-274, 1984.
Radulovacki, Miodrag, et al., "Hypotension Reduces Sleep Apneas in Zucker Lean and Zucker Obese Rats," *Sleep*, vol. 19, No. 10, pp. 767-773, 1996.
Radulovacki, Miodrag, et al., "Serotonin 5-$HT_3$-receptor Antagonist GR 38032F Suppresses Sleep Apneas in Rats," *Sleep*, vol. 21, No. 2, pp. 131-136, 1998.
Rose, D., et al., "Central effects of 5-HT on respiratory and hypoglossal activities in the adult cat," *Respiration Physiology*, vol. 101, pp. 59-69, 1995.
Sampson, Sanford R., et al., "Excitatory Effects of 5-Hydroxytryptamine, Veratridine and Phenyl Diguanide on Sensory Ganglion Cells of the Nodose Ganglion of the Cat," *Life Sciences*, vol. 15, pp. 2157-2165, 1975.
Sanders-Bush, Elaine, et al., "Chapter 11: 5-Hydroxytryptamine (Serotonin) Receptor Agonists and Antagonists," [No Citatioin], pp. 249-263, [No date].
Sapru, H. N., et al., "Effect of 5-Hydroxytryptamine on the Peripheral Chemoreceptors in the Rat," *Research Communications in Chemical Pathology and Pharmacology*, vol. 16, No. 2, pp. 245-250, 1977.
Sato, Takayuki, et al., "Sleep apneas and cardiac arrhythmias in freely moving rats," *Am. J. Physiol.*, vol. 259, pp. R282-R287, 1990.

Schmidt, H.S., "L-Tryptophan in the Treatment of Impaired Respiration in Sleep," *Bull. Europ. Physiopath. Resp.*, vol. 19, pp. 625-629, 1983.

Sieck, Gary C., et al., "Pneumotaxic Area Neuronal Discharge during Sleep—Waking States in the Cat," *Experimental Neurology*, vol. 67, pp. 79-102, 1980.

Sobel, Stephen V., et al., "Effect of Haloperidol on Sleep Apnea," *Am J Psychiatry*, vol. 142, No. 6, pp. 775-776, 1985.

Sullivan, Colin E., "Chapter 7: Breathing in Sleep," *Physiology in Sleep*, Academic Press, Inc., New York, NY, pp. 213-272, 1980.

Sutton, P. M. I., "The Interaction Between Reflex Apnoea and Bradycardia Produced by Injecting 5-HT into the Nodose Ganglion of the Cat," Pflügers Arch, vol. 389, pp. 181-187, 1981.

Szereda-Przestaszewska, Malgorzata, et al., "Effects of vagal and laryngeal afferents on apnoeic response to serotonin in cats," *Respiration Physiology*, vol. 101, pp. 231-237, 1995.

Thomas, Agnes J., et al., "A model of ventilatory instability induced in the unrestrained rat," *J. Appl. Physiol.*, pp. 1530-1536, 1992.

Thomas, Agnes, J., et al., "Modification of conditioned apneas in rats: evidence for cortical involvement," *J. Appl. Physiol.*, pp. 1215-1218, 1995.

Vandenplas, Yvan, "Clinical use of cisapride and its risk-benefit in paediatric patients," *European Journal of Gastroenterology & Hepatology*, vol. 10, No. 10, pp. 871-881, 1998.

Veasey, S.C., et al., "A Novel Serotonergic Compound Reduces Sleep-Disordered Breathing in the English Bulldog," *Sleep Research, Abstracts*, vol. 26, p. 529, 1997.

Veasey, Sigrid C., et al., "The Effects of Ondansetron on Sleep-Disordered Breathing in the English Bulldog," *Sleep*, vol. 24, No. 2, pp. 155-160, 2001.

Veasey, Sigrid C., et al., "The Effects of Serotonin Antagonists in an Animal Model of Sleep-Disordered Breathing," *Am J Respir Crit Care Med*, vol. 153, pp. 776-786, 1996.

Wilken, B., et al., "Treatment of apneustic respiratory disturbance with a serotonin-receptor agonist," *The Journal of Pediatrics*, vol. 130, No. 1, pp. 89-94, 1997.

Xiao, G. H., et al., "The Relationship Between Gerd and Osas and Effects of AntiReflux Therapy," *Gastroenterology*, vol. 114, No. 4, G1373, p. A336, 1998.

Yoshioka, Mitsuhiro, "Effect of a Novel 5-Hydroxytryptamine$_3$-Antagonist, GR38032F, on the 5-Hydroxytryptamine-Induced Increase in Carotid Sinus Nerve Activity in Rats," *The Journal of Pharmacology and Experimental Therapeutics*, vol. 250, No. 2, pp. 637-641, 1989.

Yoshioka, Mitsuhiro, et al., "Effect of 5-Hydroxytryptamine on External Carotid Nerve Activity and its Blockade by GR38032F in Anesthetized Rats," *Research Communication in Chemical Pathology and Pharmacology*, vol. 74, No. 1, pp. 39-45, 1991.

Yoshioka, Mitsuhiro, et al., "Pharmacological Characterization of 5-Hydroxytryptamine-Induced Apnea in the Rat," *The Journal of Pharmacology and Experimental Therapeutics*, vol. 260, No. 2, pp. 917-924, 1992.

Zucker, Irving H., et al., "Reflex Cardiovascular and Respiratory Effects of Serotonin in Conscious and Anesthetized Dogs," *Circulation Research*, vol. 47, No. 4, pp. 509-515, 1980.

\* cited by examiner

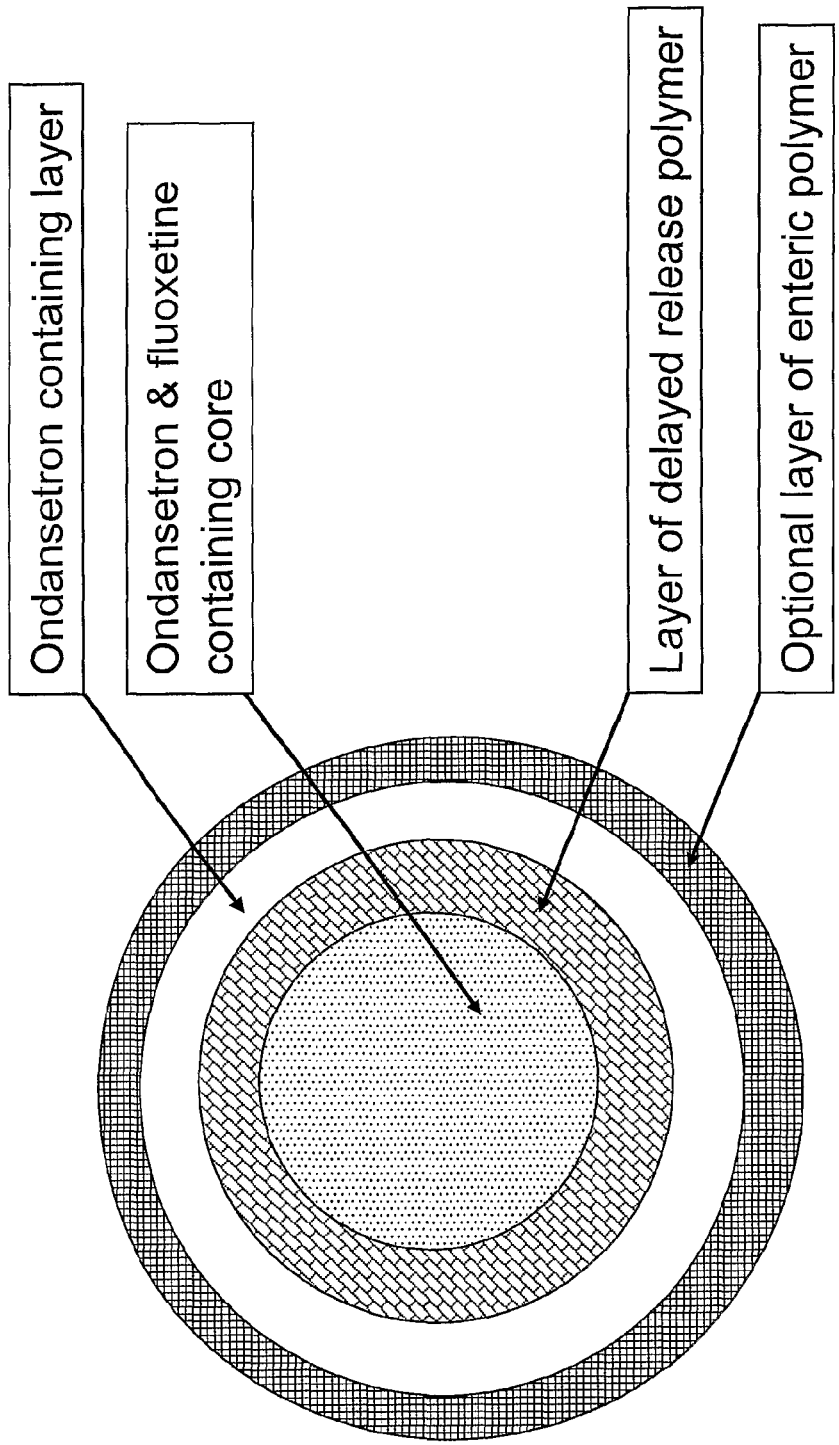
Figure 1. A multi-layer ondansetron and fluoxetine tablet formulation

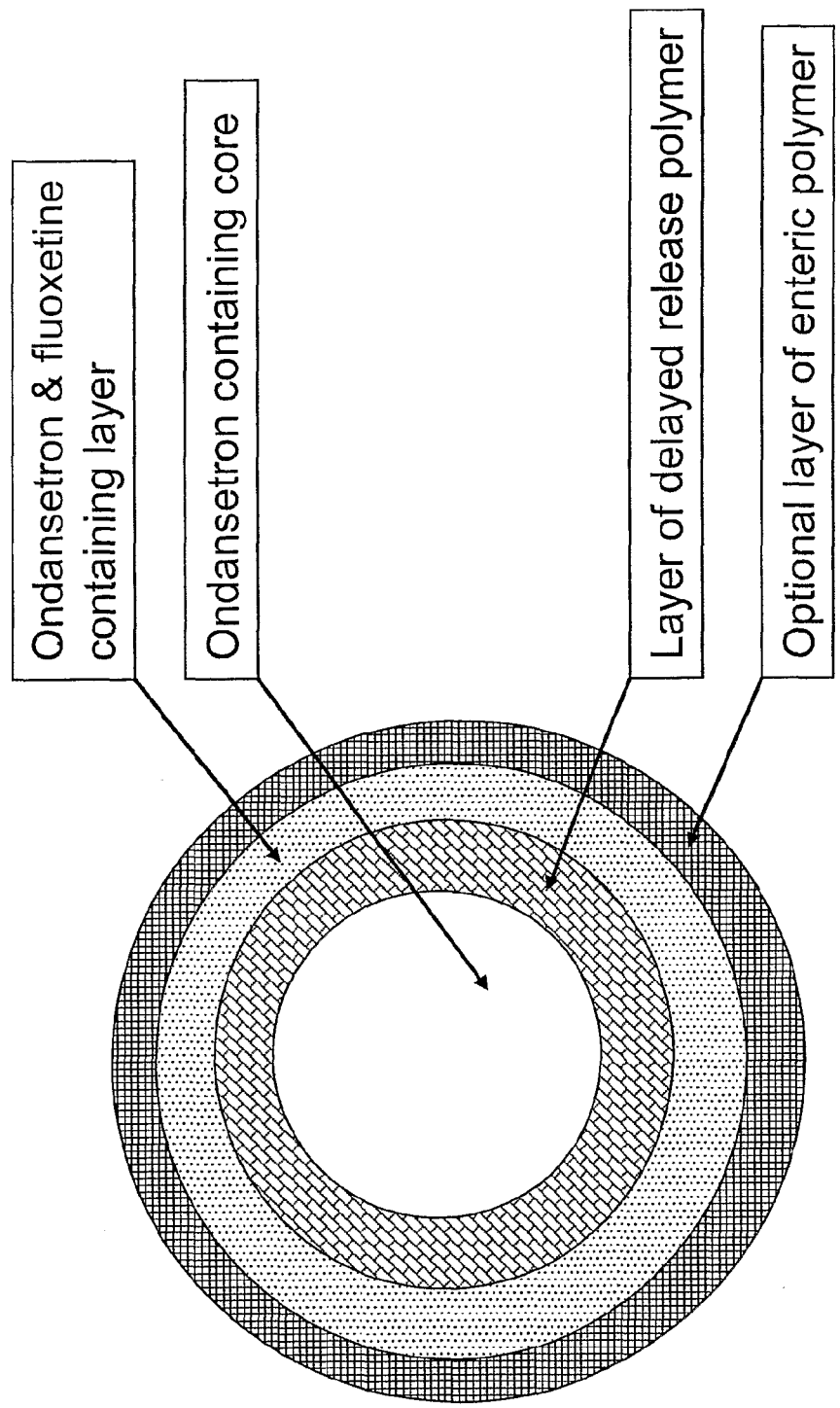
Figure 2. An alternative multi-layer ondansetron and fluoxetine tablet formulation

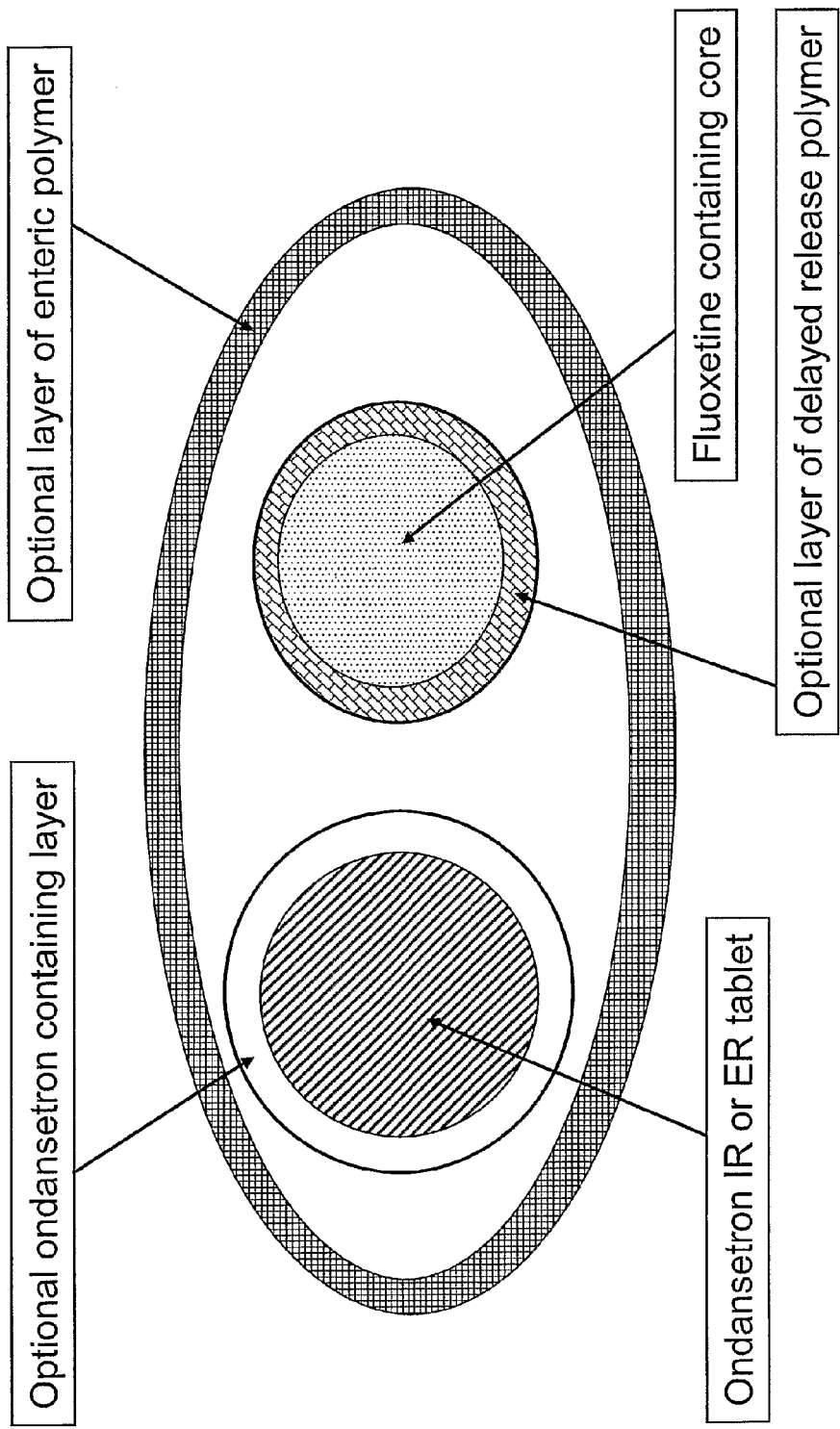
Figure 3. Ondansetron and fluoxetine capsule formulation

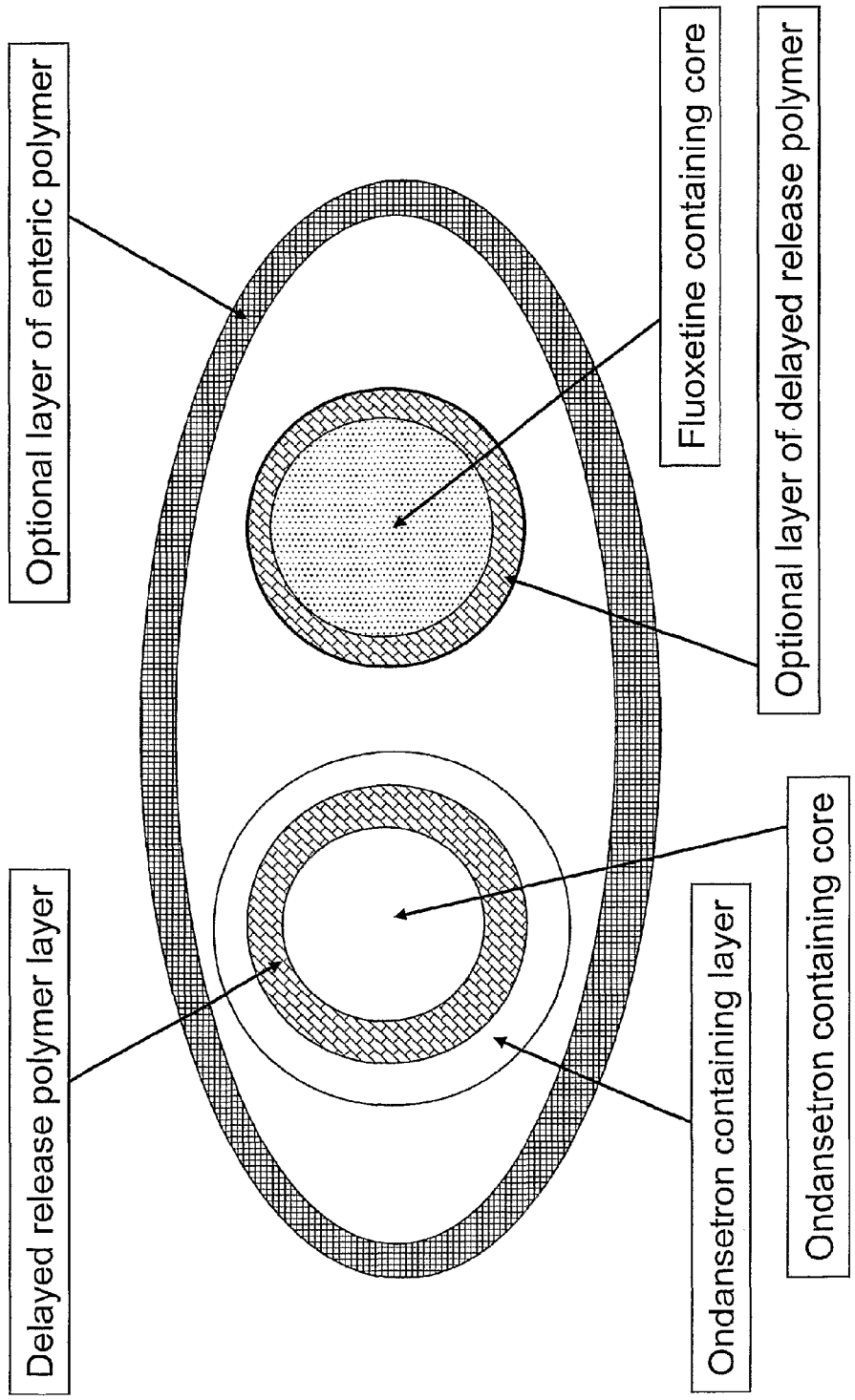
Figure 4. An alternative ondansetron and fluoxetine capsule formulation

PHARMACEUTICAL COMPOSITIONS FOR SLEEP DISORDERS

This application is a national stage filing under 35 U.S.C. §371 of International Application No. PCT/US2005/046049, filed on Dec. 20, 2005. This application claims the benefit of priority under 35 U.S.C. §119 to U.S. Provisional Application No. 60/637,655 filed on Dec. 20, 2004, the contents of each application are incorporated herein by reference.

FIELD OF THE INVENTION

This invention generally relates to pharmaceutical compositions for the pharmacological treatment of breathing disorders and, more specifically, to compositions containing agents having serotonin receptor modulating activity for the alleviation of sleep apnea (central and obstructive) and other sleep-related breathing disorders.

BACKGROUND OF THE INVENTION

Much effort has been devoted to the study of a discrete group of breathing disorders that occur primarily during sleep with consequences that may persist throughout the waking hours in the form of sleepiness, thereby manifesting itself into substantial economic loss (e.g., thousands of lost man-hours) or employment safety factors (e.g., employee non-attentiveness during operation of heavy-machinery). Sleep-related breathing disorders are characterized by repetitive reduction in breathing (hypopnea), periodic cessation of breathing (apnea), or a continuous or sustained reduction in ventilation.

In general sleep apnea is defined as an intermittent cessation of airflow at the nose and mouth during sleep. By convention, apneas of at least 10 seconds in duration have been considered important, but in most individuals the apneas are 20-30 seconds in duration and may be as long as 2-3 minutes. While there is some uncertainty as to the minimum number of apneas that should be considered clinically important, by the time most individuals come to attention of the medical community they have at least 10 to 15 events per hour of sleep.

Sleep apneas have been classified into three types: central, obstructive, and mixed. In central sleep apnea the neural drive to all respiratory muscles is transiently abolished. In obstructive sleep apneas, airflow ceases despite continuing respiratory drive because of occlusion of the oropharyngeal airway. Mixed apneas, which consist of a central apnea followed by an obstructive component, are a variant of obstructive sleep apnea. The most common type of apnea is obstructive sleep apnea.

Obstructive sleep apnea syndrome (OSAS) has been identified in as many as 24% of working adult men and 9% of similar women, with peak prevalence in the sixth decade. Habitual heavy snoring, which is an almost invariant feature of OSAS, has been described in up to 24% of middle aged men, and 14% of similarly aged women, with even greater prevalence in older subjects.

Obstructive sleep apnea syndrome's definitive event is the occlusion of the upper airway, frequently at the level of the oropharynx. The resultant apnea generally leads to a progressive-type asphyxia until the individual is briefly aroused from the sleeping state, thereby restoring airway patency and thus restoring airflow.

An important factor that leads to the collapse of the upper airway in OSAS is the generation of a critical subatmospheric pressure during the act of inspiration that exceeds the ability of the airway dilator and abductor muscles to maintain airway stability. Sleep plays a crucial role by reducing the activity of the muscles of the upper airways including the dilator and abductor muscles.

In most individuals with OSAS the patency of the airway is also compromised structurally and is therefore predisposed to occlusion. In a minority of individuals the structural compromise is usually due to obvious anatomic abnormalities, i.e, adenotonsillar hypertrophy, retrognathia, or macroglossia. However, in the majority of individuals predisposed to OSAS, the structural abnormality is simply a subtle reduction in airway size, i.e., "pharyngeal crowding." Obesity also frequently contributes to the reduction in size seen in the upper airways. The act of snoring, which is actually a high-frequency vibration of the palatal and pharyngeal soft tissues that results from the decrease in the size of the upper airway lumen, usually aggravates the narrowing via the production of edema in the soft tissues.

The recurrent episodes of nocturnal asphyxia and of arousal from sleep that characterize OSAS lead to a series of secondary physiologic events, which in turn give rise to the clinical complications of the syndrome. The most common manifestations are neuropsychiatric and behavioral disturbances that are thought to arise from the fragmentation of sleep and loss of slow-wave sleep induced by the recurrent arousal responses. Nocturnal cerebral hypoxia also may play an important role. The most pervasive manifestation is excessive daytime sleepiness. OSAS is now recognized as a leading cause of daytime sleepiness and has been implicated as an important risk factor for such problems as motor vehicle accidents. Other related symptoms include intellectual impairment, memory loss, personality disturbances, and impotence.

The other major manifestations are cardiorespiratory in nature and are thought to arise from the recurrent episodes of nocturnal asphyxia. Most individuals demonstrate a cyclical slowing of the heart during the apneas to 30 to 50 beats per minute, followed by tachycardia of 90 to 120 beats per minute during the ventilatory phase. A small number of individuals develop severe bradycardia with asystoles of 8 to 12 seconds in duration or dangerous tachyarrhythmias, including unsustained ventricular tachycardia. OSAS also aggravates left ventricular failure in patients with underlying heart disease. This complication is most likely due to the combined effects of increased left ventricular afterload during each obstructive event, secondary to increased negative intrathoracic pressure, recurrent nocturnal hypoxemia, and chronically elevated sympathoadrenal activity.

Central sleep apnea is less prevalent as a syndrome than OSAS, but can be identified in a wide spectrum of patients with medical, neurological, and/or neuromuscular disorders associated with diurnal alveolar hypoventilation or periodic breathing. The definitive event in central sleep apnea is transient abolition of central drive to the ventilatory muscles. The resulting apnea leads to a primary sequence of events similar to those of OSAS. Several underlying mechanisms can result in cessation of respiratory drive during sleep. First are defects in the metabolic respiratory control system and respiratory neuromuscular apparatus. Other central sleep apnea disorders arise from transient instabilities in an otherwise intact respiratory control system.

Many healthy individuals demonstrate a small number of central apneas during sleep, particularly at sleep onset and in REM sleep. These apneas are not associated with any physiological or clinical disturbance. In individuals with clinically significant central sleep apnea, the primary sequence of events that characterize the disorder leads to prominent physiological and clinical consequences. In those individuals with central sleep apnea alveolar hypoventilation syndrome, daytime hypercapnia and hypoxemia are usually evident and the clinical picture is dominated by a history of recurrent respiratory failure, polycythemia, pulmonary hypertension, and right-sided heart failure. Complaints of sleeping poorly, morning headache, and daytime fatigue and sleepiness are also prominent. In contrast, in individuals whose central sleep apnea results from an instability in respiratory drive, the clinical picture is dominated by features related to sleep disturbance, including recurrent nocturnal awakenings, morning fatigue, and daytime sleepiness.

Currently, the most common and most effective treatment, for adults with sleep apnea and other sleep-related breathing disorders are mechanical forms of therapy that deliver positive airway pressure (PAP). Under PAP treatment, an individual wears a tight-fitting plastic mask over the nose when sleeping. The mask is attached to a compressor, which forces air into the nose creating a positive pressure within the patient's airways. The principle of the method is that pressurizing the airways provides a mechanical "splinting" action, which prevents airway collapse and therefore, obstructive sleep apnea. Although an effective therapeutic response is observed in most patients who undergo PAP treatment, many patients cannot tolerate the apparatus or pressure and refuse treatment. Moreover, recent covert monitoring studies clearly demonstrate that long-term compliance with PAP treatment is very poor.

A variety of upper airway and craniofacial surgical procedures have been attempted for treatment of OSAS. Adenotonsillectomy appears to be an effective cure for OSAS in many children, but upper airway surgery is rarely curative in adult patients with OSAS. Surgical "success" is generally taken to be a 50% reduction in apnea incidence and there are no useful screening methods to identify the individuals that would benefit from the surgery versus those who would not derive a benefit.

Pharmacological treatments of several types have been attempted in patients with sleep apnea but, thus far, none have proven to be generally useful. One review of these attempts is provided by Hudgel [J. Lab. Clin. Med., 126:13-18 (1995)]. A number of compounds have been tested because of their expected respiratory stimulant properties. These include (1) acetazolamide, a carbonic anhydrase inhibitor that produced variable improvement in individuals with primary central apneas but caused an increase in obstructive apneas, (2) medroxyprogesterone, a progestin that has demonstrated no consistent benefit in OSAS, and (3) theophylline, a compound usually used for the treatment of asthma, which may benefit patients with central apnea but appears to be of no use in adult patients with obstructive apnea.

Other attempted pharmacological treatment includes the administration of adenosine, adenosine analogs and adenosine reuptake inhibitors (U.S. Pat. No. 5,075,290). Specifically, adenosine, which is a ubiquitous compound within the body and which levels are elevated in individuals with OSAS, has been shown to stimulate respiration and is somewhat effective in reducing apnea in an animal model of sleep apnea.

Other possible pharmacological treatment options for OSAS include agents that stimulate the brain activity or are opioid antagonists. Specifically, since increased cerebral spinal fluid opioid activity has been identified in OSAS, it is a logical conclusion that central stimulants or opioid antagonists would be a helpful treatment of OSAS. In reality, doxapram, which stimulates the central nervous system and carotid body chemoreceptors, was found to decrease the length of apneas but did not alter the average arterial oxygen saturation in individuals with obstructive sleep apnea. The opioid antagonist naloxone, which is known to stimulate ventilation was only slightly helpful in individuals with obstructive sleep apnea.

Because OSAS is strongly correlated with the occurrence of hypertension, agents such as angiotensin-converting enzyme (ACE) inhibitors may be of benefit in treating OSAS individuals with hypertension but this does not appear to be a viable treatment for OSAS itself.

Finally, several agents that act on neurotransmitters and neurotransmitter systems involved in respiration have been tested in individuals with OSAS. Most of these compounds have been developed as anti-depressant medications that work by increasing the activity of monoamine neurotransmitters including norepinephrine, dopamine, and serotonin. Protriptyline, a tricyclic anti-depressant, has been tested in several small trials with variable results and frequent and significant side effects. As serotonin may promote sleep and stimulate respiration, tryptophan, a serotonin precursor and selective serotonin reuptake inhibitors have been tested in individuals with OSAS.

Use of the serotonin reuptake inhibitor fluoxetine in treating apnea has been subject of patent (U.S. Pat. No. 5,356, 934), but initial evidence suggests that these compounds may yield measurable benefits in only approximately 50% of individuals with OSAS. Therefore in view of the fact that the only viable treatment for individuals suffering from sleep-related breathing disorders is a mechanical form of therapy (PAP) for which patient compliance is low, and that hopes for pharmacological treatments have yet to come to fruition, there remains a need for simple pharmacologically-based treatments that would offer benefits to a broad base of individuals suffering from a range of sleep-related breathing disorders. There also remains a need for a viable treatment of sleep-related breathing disorders that would lend itself to a high rate of patient compliance.

More recently, the use of serotonin receptor antagonists in the treatment of sleep apnea is disclosed in U.S. Pat. Nos. 6,331,536 and 6,727,242. These patents also disclose a combination of serotonin receptor antagonists and agonists. U.S. Pat. No. 6,727,242 also discloses the use of a combination of serotonin receptor antagonist (particularly ondansetron), and a selective serotonin reuptake inhibitor (SSRI) for the treatment of sleep apnea.

There remains a need to provide formulations that enable efficacious concentrations of the actives over the period of sleep. Some active agents have unfavorable pharmacokinetics that would require very high doses prior to sleep, or dosing during the sleep period.

The present invention provides modified release pharmaceutical compositions that provide such therapy over the sleep period and further provides such therapy in single compositions or multiple dosage forms for administration in coordinated dosage regimen with each other.

SUMMARY OF THE INVENTION

Orally administrable pharmaceutical compositions for the pharmacological treatment of breathing disorders are provided. More specifically, compositions containing serotonin receptor antagonists for the alleviation of sleep apnea (central and obstructive) and other sleep-related breathing disorders have been developed. One preferred composition comprises a serotonin receptor antagonist and an SSRI. One preferred serotonin receptor antagonist is ondansetron. One preferred SSRI is fluoxetine. Another embodiment comprises a serotonin receptor antagonist and an SNRI, preferably ondansetron and milnacipran. Another embodiment comprises a serotonin receptor antagonist and a serotonin receptor agonist. In some preferred embodiments the ondansetron release is modified in order to maintain drug plasma levels within the therapeutic range for up to 12 hours. Preferably, the formulation of ondansetron yields a release profile which compensates for the relatively short (3-5 hours) plasma half-life of ondansetron by providing ondansetron release for up to 12 hours. The release of the SSRI, SNRI, or serotonin receptor agonist is optionally delayed in order to minimize sleep disturbances. Kits are provided which contain the dosage units and instructions. Methods are also provided for the treatment and amelioration of breathing disorders.

In a first aspect of the present invention there is provided a pharmaceutical composition for providing modified release of a serotonin receptor antagonist wherein the release of antagonist provides a therapeutically effective level of antagonist in the blood plasma of a subject in need of serotonin receptor antagonism over a continuous period approximating to a period of sleep by said subject. Preferably the continuous period is at least 4 hours and is no longer than 1 hour beyond the sleep period.

Particularly the period of antagonism is provided over a period ranging from 6 to 14 hours from administration of the composition, more preferably from 7 to 12 hours and most preferably from 8 to 10 hours from administration.

Particularly the pharmaceutical provides such therapeutically effective level initiated at from 0 to 2 hours from administration of the composition and extending to between 6 and 14 hours from administration of the composition, still more preferably a continous period initiated at from 15 minutes to 1.5 hours from administration of the composition and extending to between 7 and 12 hours from administration of the composition, still more preferably initiated at from 15 minutes to 1.5 hours and extending to 8 to 10 hours from andministration.

A second aspect of the present invention provides a pharmaceutical composition containing a combination of serotonin receptor antagonist and at least one of an SSRI, a serotonin and norepinephrine reuptake inhibitor (SNRI), and a serotonin receptor agonist, that produce a therapeutic effect when administered to a patient in need, wherein the release rate and dosage are effective to provide relief from a sleep-related breathing disorder.

The serotonin receptor antagonist is preferably one having a plasma half life of less than 6 hours, more preferably of 3 to 5 hours and most preferably being ondansetron or an analogue thereof.

The SSRI, serotonin and norepinephrine reuptake inhibitor or serotonin receptor antagonist is fluoxetine.

These compositions of the second aspect provide the serotonin receptor antagonist release profile of the first aspect, together with a therapeutically effective blood plasma level of said serotonin and norepinephrine reuptake inhibitor (SNRI), and a serotonin receptor agonist over the sleep period. This level may be maintained over the whole period of treatmet, both sleep and wake, as such actives tend to have relatively long half-lives.

BRIEF DESCRIPTION OF THE DRAWINGS

FIG. 1 is a depiction of a tablet formulation of the present invention, showing a core of ondansetron and fluoxetine surrounded by a coating of polymers, further surrounded by a coating comprising ondansetron. Tie tablet is optionally further coated with an enteric polymer resulting in no drug being released in the acidic environment of the stomach.

FIG. 2 is a depiction of a tablet formulation of the present invention, showing a core of ondansetron surrounded by a coating of polymers, further surrounded by a coating comprising ondansetron and fluoxetine. The tablet is optionally further coated with an enteric polymer resulting in no drug being released in the acidic environment of the stomach.

FIG. 3 is a depiction of a capsule formulation of the present invention, showing a capsule containing ondansetron tablet and fluoxetine tablet. Ondansetron tablet is optionally an extended release tablet. Ondansetron extended release tablet is optionally surrounded by a coating comprising ondansetron. Fluoxetine tablet consists of a core optionally surrounded by a coating of polymers. It is understood that by varying polymer composition used for tablet coating, time of fluoxetine release can be altered. The capsule is optionally further coated with an enteric polymer resulting in no drug being released in the acidic environment of the stomach.

FIG. 4 is a depiction of a capsule formulation of the present invention, showing a capsule containing ondansetron tablet and fluoxetine tablet. Ondansetron tablet consists of ondansetron core surrounded by a coating of polymers, further surrounded by a coating comprising ondansetron. Fluoxetine tablet consists of a core optionally surrounded by a coating of polymers. It is understood that by varying polymer composition used for tablet coating, fluoxetine release can occur either simultaneously with the release of second pulse of ondansetron or at a different time. The capsule is optionally further coated with an enteric polymer resulting in no drug being released in the acidic environment of the stomach.

DETAILED DESCRIPTION OF THE INVENTION

The present invention is directed to pharmaceutical formulations for the prevention or amelioration of sleep-related breathing disorders, the formulations comprising effective doses of serotonin receptor antagonists with serotonin receptor agonists and/or SSRIs and/or serotonin and norepinephrine reuptake inhibitors (SNRIs). The formulations are suitable for administration to a patient in need of such therapy. The combination's constituents may be directed to a single serotonin receptor subtype or to more than one serotonin receptor subtype.

Routes of administration for the foregoing methods may be by any systemic means including oral, intraperitoneal, subcutaneous, intravenous, intramuscular, transdermal, or by other routes of administration. Osmotic mini-pumps and timed-released pellets or other depot forms of administration may also be used. The only limitation being that the route of administration results in the ultimate delivery of the pharmacological agent to the appropriate receptor.

Sleep-related breathing disorders include, but are not limited to, obstructive sleep apnea syndrome, apnea of prematurity, congenital central hypoventilation syndrome, obesity hypoventilation syndrome, central sleep apnea syndrome, Cheyne-Stokes respiration, and snoring.

A serotonin receptor antagonist can be used in its free base form or as a quaternary ammonium salt form. The quaternization of these serotonin receptor antagonists occurs by conversion of tertiary nitrogen atom into a quaternary ammonium salt with reactive alkyl halides such as, for example, methyl iodide, ethyl iodide, or various benzyl halides. Some quaternary forms of a serotonin antagonist, specifically, methylated zatosetron, has been shown to lack the ability to cross the blood-brain barrier (Gidda et al., J. Pharmacol. Exp. Ther. 273:695-701 (1995)), and thus only works on the peripheral nervous system. A serotonin receptor antagonist is defined by the chemical compound itself and one of its pharmaceutically acceptable salts.

1. Definitions

A "delayed release dosage form" is one that releases a drug (or drugs) at a time other than promptly after administration.

An "extended release dosage form" is one that allows at least a twofold reduction in dosing frequency as compared to the drug presented as a conventional dosage form (e.g. as a solution or prompt drug-releasing, conventional solid dosage form).

A "pulsatile release dosage form" is one that mimics a multiple dosing profile without repeated dosing and allows at least a twofold reduction in dosing frequency as compared to that drug presented as a conventional dosage form (e.g. as a solution or prompt drug-releasing, conventional solid dosage form). A pulsatile release profile is characterized by a time period of no release (lag time) followed by rapid drug release.

A "modified release dosage form" is one for which the drug release characteristics of time, course and/or location are chosen to accomplish therapeutic or convenience objectives not offered by conventional dosage forms such as solutions, ointments, or promptly dissolving dosage forms. Delayed release and extended release dosage forms and their combinations are types of modified release dosage forms. The pharmaceutical combination of the invention may have any or all of its constituents in a modified release dosage form. A "modifed release pharmaceutical composition" has at least one of its components in modified release dosage form.

As used herein "active compounds" in addition to their free base and quaternized forms also encompasses pharmaceutically acceptable, pharmacologically active derivatives of active compounds including individual enantiomers and their pharmaceutically acceptable salts, mixtures of enantiomers and their pharmaceutically acceptable salts, and active metabolites of active compounds and their pharmaceutically acceptable salts, unless otherwise noted. It is understood that in some cases dosages of enantiomers, derivatives, and metabolites may need to be adjusted based on relative activity of the racemic mixture of active compound.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, tolunesulfonic, methanesulfonic, ethane disulfonic, oxalic, and isethionic.

The pharmaceutically acceptable salts of the compounds can be synthesized from the parent compound, which contains a basic or acidic moiety, by conventional chemical methods.

Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in Remington's Pharmaceutical Sciences, 20th ed., Lippincott Williams & Wilkins, Baltimore, Md., 2000, p. 704.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

As used herein, the term "stereoisomers" refers to compounds made up of the same atoms bonded by the same bonds but having different spatial structures which are not interchangeable. The three-dimensional structures are called configurations. As used herein, the term "enantiomers" refers to two stereoisomers whose molecules are nonsuperimposable mirror images of one another. As used herein, the term "optical isomer" is equivalent to the term "enantiomer". The terms "racemate", "racemic mixture" or "racemic modification" refer to a mixture of equal parts of enantiomers. The term "chiral center" refers to a carbon atom to which four different groups are attached. The term "enantiomeric enrichment" as used herein refers to the increase in the amount of one enantiomer as compared to the other. Enantiomeric enrichment is readily determined by one of ordinary skill in the art using standard techniques and procedures, such as gas or high performance liquid chromatography with a chiral column. Choice of the appropriate chiral column, eluent and conditions necessary to effect separation of the enantiomeric pair is well within the knowledge of one of ordinary skill in the art using standard techniques well known in the art, such as those described by J. Jacques, et al., "Enantiomers, Racemates, and Resolutions", John Wiley and Sons, Inc., 1981. Examples of resolutions include recrystallization of diastereomeric salts/derivatives or preparative chiral chromatography.

2. Serotonin Receptor Antagonists

Exemplary serotonin receptor antagonists include, but are not limited to, the free base form or a quaternized form of zatosetron, tropisetron, dolasetron, hydrodolasetron, mescaline, oxetorone, homochlorcyclizine, perlapine, ondansetron, ketanserin, loxapine, olanzapine, chlorpromazine, haloperidol, r (+) ondansetron, cisapride, norcisapride, (+) cisapride, (−) cisapride, (+) norcisapride, (−) norcisapride, desmethylolanzapine, 2-hydroxymethylolanzapine, 1-(2-fluorophenyl)-3-(4-hydroxyaminoethyl)-prop-2-en-1-one-O-(2-dimethyla-minoethyl)-oxime, risperidone, cyproheptadine, clozapine, methysergide, granisetron, mianserin, ritanserin, cnanserin, LY-53,857, metergoline, LY-278,584, methiothepin, p-NPPL, NAN-190, piperazine, SB-206553, SDZ-205,557, 3-tropanyl-indole-3-carboxylate, 3-tropanyl-indole-3-carboxy-late methiodide, and other serotonin receptor antagonists and their quaternized forms or their pharmaceutically acceptable salts. A preferred serotonin receptor antagonist is ondansetron.

2.1 Ondansetron (CAS#116002-70-1)

Ondansetron hydrochloride (HCl) as the dihydrate, the racemic form of ondansetron and a selective blocking agent of the serotonin 5-HT 3 receptor type. Ondansetron HCl dihydrate is a white to off-white powder that is soluble in water and normal saline. Chemically it is (±) 1,2,3,9-tetrahydro-9-methyl-3-[(2-methyl-1H-imidazol-1-yl)methyl]-4H- carbazol-4-one, monohydrochloride, dihydrate. The empirical formula is C18H19N3O.HCl-2H2O, representing a molecular weight of 365.9.

Ondansetron is well absorbed from the gastrointestinal tract and undergoes some first-pass metabolism. Mean bioavailability in healthy subjects, following administration of a single 8-mg tablet, is approximately 56%. Ondansetron systemic exposure does not increase proportionately to dose. AUC from a 16-mg tablet was 24% greater than predicted from an 8-mg tablet dose. This may reflect some reduction of first-pass metabolism at higher oral doses. Bioavailability is also slightly enhanced by the presence of food but unaffected by antacids. Ondansetron half-life in humans is 3-5 hours.

Ondansetron is extensively metabolized in humans, with approximately 5% of a radiolabeled dose recovered from the urine as the parent compound. The primary metabolic pathway is hydroxylation on the indole ring followed by subsequent glucuronide or sulfate conjugation. Although some nonconjugated metabolites have pharmacologic activity, these are not found in plasma at concentrations likely to significantly contribute to the biological activity of ondansetron.

Gender differences were shown in the disposition of ondansetron given as a single dose. The extent and rate of ondansetron's absorption is greater in women than men. Slower clearance in women, a smaller apparent volume of distribution (adjusted for weight), and higher absolute bioavailability resulted in higher plasma ondansetron levels. These higher plasma levels may in part be explained by differences in body weight between men and women. It is not known whether these gender-related differences were clinically important.

More information about clinical pharmacology of ondansetron can be found in 2005 issue of Physician Desk Reference under Zofran® trade name (GlaxoSmithKline).

3. Serotonin Receptor Agonists

Exemplary serotonin receptor agonists include, but are not limited to 8-OH-DPAT, sumatriptan, L694247 (2-[5-[3-(4-methylsulphonylamino)benzy-1-1,2,4-oxadiazol-5-yl]-1H-indol-3yl]ethanamine), buspirone, alnitidan, zalospirone, ipsapirone, gepirone, zolmitriptan, risatriptan, 311C90, .alpha.-Me-5-HT, BW723C86 (1-[5(2-thienylmethoxy)-1H-3-indolyl[propan-2-a-mine hydrochloride), and MCPP (m-chlorophenylpiperazine). A serotonin receptor agonist is defined by the chemical compound itself and one of its pharmaceutically acceptable salts. Preferred serotonin receptor agonists include buspirone, zolmitriptan, and risatriptan.

4. Selective Serotonin Reuptake Inhibitors

Exemplary selective serotonin reuptake inhibitors include, but are not limited to, fluoxetine, paroxetine, fluvoxamine, sertraline, citalopram, norfluoxetine, r(−) fluoxetine, s(+) fluoxetine, demethylsertraline, demethylcitalopram, venlafaxine, milnacipran, sibutramine, nefazodone, R-hydroxynefazodone, (−) venlafaxine, and (+) venlafaxine. A selective serotonin reuptake inhibitor is defined by the chemical compound itself and one of its pharmaceutically acceptable salts. Preferred SSRIs include fluoxetine, paroxetine, and milnacipran.

4.1 Fluoxetine (CAS#54910-89-3)

Fluoxetine hydrochloride is a psychotropic drug for oral administration. It is also marketed for the treatment of premenstrual dysphoric disorder (Sarafem®, fluoxetine hydrochloride). It is designated (±)-N-methyl-3-phenyl-3-[((alpha),(alpha),(alpha)-trifluoro-p-tolyl)oxy]propylamine hydrochloride and has the empirical formula of C17H18F3NOHCl. Its molecular weight is 345.79. Fluoxetine hydrochloride is a white to off-white crystalline solid with a solubility of 14 mg/mL in water.

In man, following a single oral 40-mg dose, peak plasma concentrations of fluoxetine from 15 to 55 ng/mL are observed after 6 to 8 hours. Fluoxetine is extensively metabolized in the liver to norfluoxetine and a number of other unidentified metabolites. The only identified active metabolite, norfluoxetine, is formed by demethylation of fluoxetine. In animal models, S-norfluoxetine is a potent and selective inhibitor of serotonin uptake and has activity essentially equivalent to R- or S-fluoxetine. R-norfluoxetine is significantly less potent than the parent drug in the inhibition of serotonin uptake. The primary route of elimination appears to be hepatic metabolism to inactive metabolites excreted by the kidney.

Fluoxetine effects sleep architecture by suppressing rapid eye movement sleep and increasing nocturnal arousals. In the study aimed at investigating the effects of fluoxetine (20, 40 and 60 mg), on nocturnal sleep and on alertness during the day in healthy adults, drug reduced the total sleep time and the duration of rapid eye movement (REM) sleep and increased awake activity and stage 1 (drowsy) sleep during the night. It was suggested that the serotonergic system has a pervasive influence throughout the sleep-wakefulness continuum (Nicholson, A. N. and Pascoe, P. A., Neuropharmacology, 1988, 27(6):597-602).

In another study, fluoxetine treatment significantly increases the number of eye movements and the amplitude of EOG and EMG activity increased significantly on treatment in REM, stages 1, 2, and slow-wave sleep. All patients showed EOG and EMG abnormalities in at least one stage of sleep. Thirty-four percent of patients showed increased EOG and EMG activity on treatment in every sleep stage. It is suggested that fluoxetine-induced oculomotor abnormalities are likely to be the result of increased availability of serotonin and secondary dopaminergic effects (Armitage R, et al., Neuropsychopharmacology, 1995, 12(2):159-165).

More information about clinical pharmacology of fluoxetine can be found in 2005 issue of Physician Desk Reference under Prozac® trade name (Lilly).

5. Serotonin and Norepinephrine Reuptake Inhibitors

Exemplary SNRIs include, milnacipran, venlafaxine, duloxetine. Preferred SNRI is milnacipran.

A preferred combination of the invention is ondansetron and modified release fluoxetine. Another preferred combination of the invention is modified release ondansetron and immediate release fluoxetine. Another preferred combination of the invention is modified release ondansetron and modified release fluoxetine. Another preferred embodiment is ondansetron and modified release paroxetine. Yet another preferred embodiment is modified release ondansetron and modified release paroxetine. A further preferred embodiment is ondansetron and modified release milnacipran. Alternative preferred embodiments are those in which the ondansetron component is in modified release dosage form, together with fluoxetine or paroxetine or milnacipran, in conventional or modifed release dosage form.

6. Combinations with Other Active Compounds

The pharmaceutical combination of serotonin receptor antagonist and serotonin receptor agonist, or serotonin receptor antagonist and SSRI can be administered adjunctively with other active compounds such as analgesics, anti-inflammatory drugs, antipyretics, antidepressants, antiepileptics, antihistamines, antimigraine drugs, antimuscarinics, anxiolytics, sedatives, hypnotics, antipsychotics, bronchodilators, anti asthma drugs, cardiovascular drugs, corticosteroids, dopaminergics, electrolytes, gastro-intestinal drugs, muscle relaxants, nutritional agents, vitamins, parasympathomimetics, stimulants, anorectics and anti-narcoleptics.

Specific examples of compounds that can be adjunctively administered with ondansetron or ondansetron-fluoxetine combination include, but are not limited to, aceclofenac, acetaminophen, almotriptan, alprazolam, amantadine, amcinonide, aminocyclopropane, amitriptyline, amlodipine, amoxapine, amphetamine, aripiprazole, aspirin, atomoxetine, azasetron, azatadine, beclomethasone, benactyzine, benoxaprofen, bermoprofen, betamethasone, bicifadine, bromocriptine, budesonide, buprenorphine, bupropion, buspirone, butorphanol, butriptyline, caffeine, carbamazepine, carbidopa, carisoprodol, celecoxib, chlordiazepoxide, chlorpromazine, choline salicylate, citalopram, clomipramine, clonazepam, clonidine, clonitazene, clorazepate, clotiazepam, cloxazolam, clozapine, codeine, corticosterone, cortisone, cyclobenzaprine, cyproheptadine, demexiptiline, desipramine, desomorphine, dexamethasone, dexanabinol, dextroamphetamine sulfate, dextromoramide, dextropropoxyphene, dezocine, diazepam, dibenzepin, diclofenac sodium, diflunisal, dihydrocodeine, dihydroergotamine, dihydromorphine, dimetacrine, divalproex, tizatriptan, dolasetron, donepezil, dothiepin, doxepin, duloxetine, ergotamine, escitalopram, estazolam, ethosuximide, etodolac, femoxetine, fenamates, fenoprofen, fentanyl, fludiazepam, fluoxetine, fluphenazine, flurazepam, flurbiprofen, flutazolam, fluvoxamine, frovatriptan, gabapentin, galantamine, gepirone, Ginko biloba, granisetron, haloperidol, huperzine A, hydrocodone, hydrocortisone, hydromorphone, hydroxyzine, ibuprofen, imipramine, indiplon, indomethacin, indoprofen, iprindole, ipsapirone, ketanserin, ketoprofen, ketorolac, lesopitron, levodopa, lipase, lofepramine, lorazepam, loxapine, maprotiline, mazindol, mefenamic acid, melatonin, melitracen, memantine, meperidine, meprobamate, mesalamine, metapramine, metaxalone, methadone, methamphetamine, methocarbamol, methyldopa, methylphenidate, methylsalicylate, methysergid(e), metoclopramide, mianserin, mifepristone, milnacipran, minaprine, mirtazapine, moclobemide, modafinil (an anti-narcoleptic), molindone, morphine, morphine, hydrochloride, nabumetone, nadolol, naproxen, naratriptan, nefazodone, neuronatin, nomifensine, nortriptyline, olanzapine, olsalazine, ondansetron, opipramol, orphenadrine, oxaflozane, oxaprozin, oxazepam, oxitriptan, oxycodone, oxymorphone, pancrelipase, parecoxib, paroxetine, pemoline, pentazocine, pepsin, perphenazine, phenacetin, phendimetrazine, phenmetrazine, phenylbutazone, phenytoin, phosphatidylserine, pimozide, pirlindole, piroxicam, pizotifen, pizotyline, pramipexole, prednisolone, prednisone, pregabalin, propranolol, propizepine, propoxyphene, protriptyline, quazepam, quinupramine, reboxetine, reserpine, risperidone, ritanserin, rivastigmine, rizatriptan, rofecoxib, ropinirole, rotigotine, salsalate, sertraline, sibutramine, sildenafil, sulfasalazine, sulindac, sumatriptan, tacrine, temazepam, tetrabenazine, thiazides, thioridazine, thiothixene, tiapride, tiospirone, tizanidine, tofenacin, tolmetin, toloxatone, topiramate, tramadol, trazodone, triazolam, trifluoperazine, trimethobenzamide, trimipramine, tropisetron, valdecoxib, valproic acid, venlafaxine, viloxazine, vitamin E, zimeldine, ziprasidone, zolmitriptan, zolpidem, zopiclone and isomers, salts, and combinations thereof.

By adjunctive administration is meant simultaneous administration of the compounds, in the same dosage form, simultaneous administration in separate dosage forms, and separate administration of the compounds.

7. Formulations

Formulations are prepared using a pharmaceutically acceptable "carrier" composed of materials that are considered safe and effective and may be administered to an individual without causing undesirable biological side effects or unwanted interactions. The "carrier" is all components present in the pharmaceutical formulation other than the active ingredient or ingredients. The term "carrier" includes but is not limited to diluents, binders, lubricants, desintegrators, fillers, and coating compositions.

"Carrier" also includes all components of the coating composition which may include plasticizers, pigments, colorants, stabilizing agents, and glidants. The delayed release dosage formulations may be prepared as described in references such as "Pharmaceutical dosage form tablets", eds. Liberman et. al. (New York, Marcel Dekker, Inc., 1989), "Remington—The science and practice of pharmacy", 20th ed., Lippincott Williams & Wilkins, Baltimore, Md., 2000, and "Pharmaceutical dosage forms and drug delivery systems", $6^{th}$Edition, Ansel et. al., (Media, PA: Williams and Wilkins, 1995) which provides information on carriers, materials, equipment and process for preparing tablets and capsules and delayed release dosage forms of tablets, capsules, and granules.

Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name Eudragit® (Roth Pharma, Westerstadt, Germany), Zein, shellac, and polysaccharides.

Additionally, the coating material may contain conventional carriers such as plasticizers, pigments, colorants, glidants, stabilization agents, pore formers and surfactants.

Optional pharmaceutically acceptable excipients present in the drug-containing tablets, beads, granules or particles include, but are not limited to, diluents, binders, lubricants, disintegrants, colorants, stabilizers, and surfactants. Diluents, also termed "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powder sugar.

Binders are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydorxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

Lubricants are used to facilitate tablet manufacture. Examples of suitable lubricants include, but are not limited to, magnesium stearate, calcium stearate, stearic acid, glycerol behenate, polyethylene glycol, talc, and mineral oil.

Disintegrants are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as crosslinked PVP (Polyplasdone XL from GAF Chemical Corp).

Stabilizers are used to inhibit or retard drug decomposition reactions which include, by way of example, oxidative reactions.

Surfactants may be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylpbenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-.beta.-alanine, sodium N-lauryl-.beta.-iminodipropionate, myristoamphoacetate, lauryl betaine and lauryl sulfobetaine.

If desired, the tablets, beads granules or particles may also contain minor amount of nontoxic auxiliary substances such as wetting or emulsifying agents, dyes, pH buffering agents, and preservatives.

The immediate release dosage unit of the dosage form—i.e., a tablet, a plurality of drug-containing beads, granules or particles, or an outer layer of a coated core dosage form—contains a therapeutically effective quantity of the active agent with conventional pharmaceutical excipients. The immediate release dosage unit may or may not be coated, and may or may not be admixed with the delayed release dosage unit or units (as in an encapsulated mixture of immediate release drug-containing granules, particles or beads and delayed release drug-containing granules or beads). A preferred method for preparing immediate release tablets (e.g., as incorporated into a capsule) is by compressing a drug-containing blend, e.g., blend of granules, prepared using a direct blend, wet-granulation or dry-granulation process. Immediate release tablets may also be molded rather than compressed, starting with a moist material containing a suitable water-soluble lubricant. However, preferred tablets herein are manufactured using compression rather than molding. A preferred method for forming immediate release drug-containing blend is to mix drug particles directly with one or more excipients such as diluents (or fillers), binders, disintegrants, lubricants, glidants, colorants or the like. As an alternative to direct blending, a drug-containing blend may be prepared by using a wet-granulation or dry-granulation processes. Beads containing the active agent may also be prepared by any one of a number of conventional techniques, typically starting from a fluid dispersion. For example, a typical method for preparing drug-containing beads involves blending the active agent with conventional pharmaceutical excipients such as microcrystalline cellulose, starch, polyvinylpyrrolidone, methylcellulose, talc, metallic stearates, silicone dioxide, or the like. The admixture is used to coat a bead core such as a sugar sphere (or so-called "non-pareil") having a size of approximately 20 to 60 mesh.

An alternative procedure for preparing drug beads is by blending drug with one or more pharmaceutically acceptable excipients, such as microcrystalline cellulose, lactose, cellulose, polyvinyl pyrrolidone, talc, magnesium stearate, a disintegrant, etc., extruding the blend, spheronizing the extrudate, drying and optionally coating to form the immediate release beads.

The amount of active agent released in each dose will be a therapeutically effective amount.

7.1 Delayed Release Dosage Forms

Delayed release formulations are created by coating a solid dosage form with a polymer film, which is insoluble in the acidic environment of the stomach, and soluble in the neutral environment of the small intestine.

The delayed release dosage units can be prepared, for example, by coating a drug or a drug-containing composition with a selected coating material. The drug-containing composition may be, e.g., a tablet for incorporation into a capsule, a tablet for use as an inner core in a "coated core" dosage form, or a plurality of drug-containing beads, particles or granules, for incorporation into either a tablet or capsule. Preferred coating materials include bioerodible, gradually hydrolyzable, gradually water-soluble, and/or enzymatically degradable polymers, and may be conventional "enteric" polymers. Enteric polymers, as will be appreciated by those skilled in the art, become soluble in the higher pH environment of the lower gastrointestinal tract or slowly erode as the dosage form passes through the gastrointestinal tract, while enzymatically degradable polymers are degraded by bacterial enzymes present in the lower gastrointestinal tract, particularly in the colon. Suitable coating materials for effecting delayed release include, but are not limited to, cellulosic polymers such as hydroxypropyl cellulose, hydroxyethyl cellulose, hydroxymethyl cellulose, hydroxypropyl methyl cellulose, hydroxypropyl methyl cellulose acetate succinate, hydroxypropylmethyl cellulose phthalate, methylcellulose, ethyl cellulose, cellulose acetate, cellulose acetate phthalate, cellulose acetate trimellitate and carboxymethylcellulose sodium; acrylic acid polymers and copolymers, preferably formed from acrylic acid, methacrylic acid, methyl acrylate, ethyl acrylate, methyl methacrylate and/or ethyl methacrylate, and other methacrylic resins that are commercially available under the tradename Eudragit®. (Rohm Pharma; Westerstadt, Germany), including Eudragit® L30D-55 and L100-55 (soluble at pH 5.5 and above), Eudragit® L-100 (soluble at pH 6.0 and above), Eudragit® S (soluble at pH 7.0 and above, as a result of a higher degree of esterification), and Eudragits NE, RL and RS (water-insoluble polymers having different degrees of permeability and expandability); vinyl polymers and copolymers such as polyvinyl pyrrolidone, vinyl acetate, vinylacetate phthalate, vinylacetate crotonic acid copolymer, and ethylene-vinyl acetate copolymer; enzymatically degradable polymers such as azo polymers, pectin, chitosan, amylose and guar gum; zein and shellac. Combinations of different coating materials may also be used. Multi-layer coatings using different polymers may also be applied. Polymer blends can be used to achieve the desired delay in drug release.

The preferred coating weights for particular coating materials may be readily determined by those skilled in the art by evaluating individual release profiles for tablets, beads and granules prepared with different quantities of various coating materials. It is the combination of materials, method and form of application that produce the desired release characteristics, which one can determine only from the clinical studies.

The coating composition may include conventional additives, such as plasticizers, pigments, colorants, stabilizing agents, glidants, etc. A plasticizer is normally present to reduce the fragility of the coating, and will generally represent about 10 wt. % to 50 wt. % relative to the dry weight of the polymer. Examples of typical plasticizers include polyethylene glycol, propylene glycol, triacetin, dimethyl phthalate, diethyl phthalate, dibutyl phthalate, dibutyl sebacate, triethyl citrate, tributyl citrate, triethyl acetyl citrate, castor oil and acetylated monoglycerides. A stabilizing agent is preferably used to stabilize particles in the dispersion. Typical stabilizing agents are nonionic emulsifiers such as sorbitan esters, polysorbates and polyvinylpyrrolidone. Glidants are recommended to reduce sticking effects during film formation and drying, and will generally represent approximately 25 wt. % to 100 wt. % of the polymer weight in the coating solution. One effective glidant is talc. Other glidants such as magnesium stearate and glycerol monostearates may also be used. Pigments such as titanium dioxide may also be used. Small quantities of an anti-foaming agent, such as a silicone (e.g., simethicone), may also be added to the coating composition.

7.2 Pulsatile Release Dosage Forms

Pulsatile release of active ingredients may be achieved by coating the active ingredients with polymers chosen to release the second and any further pulses at specific time points. This embodiment of the invention allows for the administration of a dosage form which provides a first release (pulse) of active ingredient, followed by a desired delay before a second pulse of active ingredient. The polymers are chosen in such a way as to deliver the secondary pulses at chosen time intervals. The time intervals may be chosen based on the pharmacokinetics of the desired plasma level of the active ingredient, and/or may be chosen based on the release site of the second pulse.

The composition provides an initial rapid release of a therapeutically effective dose of ondansetron followed by so-called "delayed release" pulses such that a second and optional third delayed dose of the active agent is released from the dosage form. By incorporating both an immediate release dosage unit and one or more delayed release dosage units of the active agent, the dosage form mimics a multiple dosing profile without repeated dosing, i.e., with only a single administration. For example, the dosage form provides a twice daily dosing profile when the dosage form contains both an immediate release dosage unit and a single delayed release dosage unit. Alternatively, the dosage form provides a three times daily dosing profile when the dosage form contains an immediate release dosage unit and two delayed release dosage units. The formulation provides a pulsatile release dosage form, wherein the dosage form comprises an immediate release dosage unit, a delayed release dosage unit and an optional second delayed release dosage unit. The immediate release dosage unit comprises a first dose of an active agent that is released substantially immediately following oral administration of the dosage form to a patient. The delayed release dosage unit comprises a second dose of the active agent and a means for delaying release of the second dose until approximately 3 hours to less than 14 hours following oral administration of the dosage form. The second delayed release dosage unit, when present, comprises a third dose of the active agent and a means for delaying release of the third dose until at least 5 hours to approximately 18 hours following oral administration of the dosage form.

Each dosage form contains a therapeutically effective amount of active agent. For dosage forms that mimic the twice daily dosing profile, approximately 30 wt. % to 80 wt. %, preferably 40 wt. % to 70 wt. %, of the total amount of active agent in the dosage form is released in the initial pulse, and, correspondingly approximately 70 wt. % to 20 wt. %, preferably 60 wt. % to 30 wt. %, of the total amount of active agent in the dosage form is released in the second pulse. For dosage forms mimicking the twice daily dosing profile, the second pulse is preferably released approximately 3 hours to less than 14 hours, and most preferably approximately 5 hours to 12 hours, following administration.

For dosage forms mimicking the three times daily dosing profile, approximately 25 wt. % to 40 wt. % of the total amount of active agent in the dosage form is released in the initial pulse, and approximately 25 wt. % to 40 wt. % of the total amount of active agent in the dosage form is released in each of the second and third pulses. For dosage forms that mimic the three times daily dosing profile, release of the second pulse preferably takes place approximately 3 hours to 10 hours, and most preferably approximately 4 to 9 hours, following oral administration. Release of the third pulse occurs about 2 hours to about 8 hours following the second pulse, and is typically about 5 hours to approximately 18 hours following oral administration.

In one aspect, a dosage form comprising a closed capsule housing at least two drug-containing dosage units is used. Each dosage unit comprises two or more compressed tablets, or may be comprised of a plurality of beads, granules or particles, providing that each dosage unit has a different drug release profile. The immediate release dosage unit releases drug substantially immediately following oral administration to provide an initial dose. The delayed release dosage unit releases drug approximately 3 hours to 14 hours following oral administration to provide a second dose. Finally, an optional second delayed release dosage unit releases drug about 2 hours to 8 hours following the release of the second dose, and is typically 5 hours to 18 hours following oral administration.

Another dosage form comprises a compressed tablet having a drug-containing immediate release dosage unit, a delayed release dosage unit and an optional second delayed release dosage unit. In this dosage form, the immediate release dosage unit comprises a plurality of beads, granules or particles that release drug substantially immediately following oral administration to provide an initial dose. The delayed release dosage unit comprises a plurality of coated beads or granules, which release drug approximately 3 hours to 14 hours following oral administration to provide a second dose.

An optional second delayed release dosage unit comprises coated beads or granules that release drug about 2 to 8 hours following administration of the initial delayed release dose, typically 5 to 18 hours following oral administration. The beads or granules in the delayed release dosage unit(s) are coated with a bioerodible polymeric material. This coating prevents the drug from being released until the appropriate time, i.e., approximately 3 hours to less than 14 hours following oral administration for the delayed release dosage unit and at least 5 hours to approximately 18 hours following oral administration for the optional second delayed release dosage unit. In this dosage form the components may be admixed in the tablet or may be layered to form a laminated tablet.

Another dosage form is a tablet having a drug-containing immediate release dosage unit, a delayed release dosage unit, and an optional second delayed release dosage unit, wherein the immediate release dosage unit comprises an outer layer that releases the drug substantially immediately following oral administration. The arrangement of the remaining delayed release dosage(s), however, depends upon whether the dosage form is designed to mimic twice daily dosing or three times daily dosing.

In the dosage form mimicking twice daily dosing, the delayed release dosage unit comprises an inner core that is coated with a bioerodible polymeric material. The coating is applied such that release of the drug occurs approximately 3 hours to less than 14 hours following oral administration. In this form, the outer layer completely surrounds the inner core. In the dosage form mimicking three times a day dosing, the (first) delayed release dose comprises an internal layer that releases drug approximately 3 hours to less than 14 hours following oral administration. This internal layer is surrounded by the outer layer. The second delayed release dosage unit generally comprises an inner core that releases the drug at least 5 hours to approximately 18 hours following oral administration. Thus, the layers of this tablet (starting from the external surface) comprise an outer layer, an internal layer and an inner core. The inner core comprises delayed release beads or granules. Furthermore, the internal layer comprises the drug coated with a bioerodible polymeric material. Alternatively, in this particular dosage form mimicking three times a day dosing, both the delayed release dosage unit and second delayed release dosage units are surrounded by an inner layer. This inner layer is free of active agent. Thus, the layers of this tablet (starting from the external surface) comprise an outer layer, inner layer and an admixture of the delayed release dosage units. The first delayed release pulse occurs once the inner layer is substantially eroded thereby releasing the admixture of the delayed release dosage units. The dose corresponding to the (first) delayed release dosage unit is released immediately since the inner layer has prevented access to this dose for the appropriate time, e.g., from approximately 3 hours to 10 hours. The second delayed release dose, however, is formulated to effectively delay release for at least 5 hours to approximately 18 hours following oral administration.

Alternatively, each dosage unit in the capsule may comprise a plurality of drug-containing beads, granules or particles. As is known in the art, drug-containing "beads" refer to beads made with drug and one or more excipients or polymers. Drug-containing beads can be produced by applying drug to an inert support, e.g., inert sugar beads coated with drug or by creating a "core" comprising both drug and one or more excipients. As is also known, drug-containing "granules" and "particles" comprise drug particles that may or may not include one or more additional excipients or polymers. In contrast to drug-containing beads, granules and particles do not contain an inert support. Granules generally comprise drug particles and require further processing. Generally, particles are smaller than granules, and are not further processed. Although beads, granules and particles may be formulated to provide immediate release, beads and granules are generally employed to provide delayed release.

In still another embodiment, a dosage form comprises a coated core-type delivery system wherein the outer layer is comprised of an immediate release dosage unit, such that active agent therein is immediately release following oral administration, an intermediate layer thereunder surrounds a core, and the core is comprised of immediate release beads or granules and delayed release beads or granules, such that the second dose is provided by the immediate release beads or granules and the third dose is provided by the delayed release beads or granules.

For the compositions of the present invention, where the second pulse is intended to be delivered, a delay of 3-8 hours is desired between the time of administration and the release of the second pulse. Appropriate polymers are chosen which release the second pulse at 3-8 hours. In this way, a series of pulses may be achieved over specific time intervals or specific release sites. The aforementioned polymers can be used to construct delayed release portion(s) of pulsatile release composition. Polymer blends can be used to achieve the desired release profile.

Thus, in one embodiment, a serotonin receptor antagonist is present in a tablet form in both an outer portion of the tablet (to achieve the first release pulse) and an inner core (to achieve a second release pulse). A preferred embodiment comprises ondansetron in the core, coated with polymers, and further coated with a composition comprising ondansetron.

Preferred polymers for coating all embodiments of the invention include Eudragit L-100, Eudragit S-100, and their mixtures wherein Eudragit L-100 to Eudragit S-100 ratio is from approximately 95/5 to approximately 75/25 (w/w), more preferably 90/10 to 80/20 (w/w), in order to achieve a second pulse at about 3-8 hours. A combination of ondansetron tablet and fluoxetine tablet in a hard gelatin capsule, wherein fluoxetine tablet is optionally coated with polymers, is depicted in FIG. 4. It is understood that by varying polymer composition used for tablet coating, fluoxetine release can occur either simultaneously with the release of second pulse of ondansetron or at a different time.

Another preferred embodiment adds a dose of fluoxetine to the inner core, such that upon administration of the tablet to a patient, a first pulse of ondansetron is followed by a pulse of ondansetron and fluoxetine 3-8 hours later. A tablet dosage form of this embodiment is depicted in FIG. 1. This embodiment releases ondansetron upon administration, followed 3-8 hours later by a release of fluoxetine and a second pulse of ondansetron. Such a form allows for the pulsatile release of ondansetron as well as the time delayed release of fluoxetine, thereby minimizing sleep disturbances related to fluoxetine administration shortly before bedtime.

Additional examples of such pulsatile release dosage forms are readily constructed based on these principles.

7.3 Extended Release Dosage Forms

The extended release formulations are generally prepared as diffusion or osmotic systems, for example, as described in "Remington—The science and practice of pharmacy" (20th ed., Lippincott Williams & Wilkins, Baltimore, Md., 2000). A diffusion system typically consists of two types of devices, a reservoir and a matrix, and is well known and described in the art. The matrix devices are generally prepared by compressing the drug with a slowly dissolving polymer carrier into a tablet form. The three major types of materials used in the preparation of matrix devices are insoluble plastics, hydrophilic polymers, and fatty compounds. Plastic matrices include, but not limited to, methyl acrylate-methyl methacrylate, polyvinyl chloride, and polyethylene. Hydrophilic polymers include, but are not limited to, cellulosic polymers such as methyl and ethyl cellulose hydroxyalkylcelluloses such as hydroxypropylcellulose, hydroxypropylmethylcellulose, sodium carboxymethylcellulose, and carbopol 934, polyethylene oxides and mixtures thereof. Fatty compounds include, but are not limited to, various waxes such as carnauba wax and glyceryl tristearate and wax-type substances including hydrogenated castor oil or hydrogenated vegetable oil, or mixtures thereof.

In certain preferred embodiments, the plastic material is a pharmaceutically acceptable acrylic polymer, including but not limited to, acrylic acid and methacrylic acid copolymers, methyl methacrylate, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamine copolymer poly(methyl methacrylate), poly(methacrylic acid)(anhydride), polymethacrylate, polyacrylamide, poly(methacrylic acid anhydride), and glycidyl methacrylate copolymers.

In certain preferred embodiments, the acrylic polymer is comprised of one or more ammonio methacrylate copolymers. Ammonio methacrylate copolymers are well known in the art, and are described in NF XVII as fully polymerized copolymers of acrylic and methacrylic acid esters with a low content of quaternary ammonium groups.

In one preferred embodiment, the acrylic polymer is an acrylic resin lacquer such as that which is commercially available from Rohm Pharma under the Tradename Eudragit.®. In further preferred embodiments, the acrylic polymer comprises a mixture of two acrylic resin lacquers commercially available from Rohm Pharma under the Tradenames Eudragit.®. RL30D and Eudragit.®. RS30D, respectively. Eudragit.®. RL30D and Eudragit.®. RS30D are copolymers of acrylic and methacrylic esters with a low content of quaternary ammonium groups, the molar ratio of ammonium groups to the remaining neutral (meth)acrylic esters being 1:20 in Eudragit.®. RL30D and 1:40 in Eudragit.®. RS30D. The mean molecular weight is about 150,000. Edragit.®. and Eudragit.®.L-100 are also preferred. The code designations RL (high permeability) and RS (low permeability) refer to the permeability properties of these agents. Eudragit.®. RL/RS mixtures are insoluble in water and in digestive fluids. However, _multiparticulate systems formed to include the same are swellable and permeable in aqueous solutions and digestive fluids.

The polymers described above such as Eudragit.®. RL/RS may be mixed together in any desired ratio in order to ultimately obtain a sustained-release formulation having a desirable dissolution profile. Desirable sustained-release multiparticulate systems may be obtained, for instance, from 100% Eudragit.®. RL, 50% Eudragit.®. RL and 50% Eudragit.®. RS, and 10% Eudragit.®. RL:Eudragit.®. 90% RS. One skilled in the art will recognize that other acrylic polymers may also be used, such as, for example, Eudragit.®. L.

Alternatively, extended release formulations can be prepared using osmotic systems or by applying a semi-permeable coating to the dosage form. In the latter case, the desired drug release profile can be achieved by combining low permeable and high permeable coating materials in suitable proportion.

The devices with different drug release mechanisms described above can be combined in a final dosage form comprising single or multiple units. Examples of multiple units include multilayer tablets, capsules containing tablets, beads, granules, etc.

An immediate release portion can be added to the extended release system by means of either applying an immediate release layer on top of the extended release core using a coating or compression process or in a multiple unit system such as a capsule containing extended and immediate release beads.

Extended release tablets containing hydrophilic polymers are prepared by techniques commonly known in the art such as direct compression, wet granulation, or dry granulation processes. Their formulations usually incorporate polymers, diluents, binders, and lubricants as well as the active pharmaceutical ingredient. The usual diluents include inert powdered substances such as starches, powdered cellulose, especially crystalline and microcrystalline cellulose, sugars such as fructose, mannitol and sucrose, grain flours and similar edible powders. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders include substances such as starch, gelatin and sugars such as lactose, fructose, and glucose. Natural and synthetic gums, including acacia, alginates, methylcellulose, and polyvinylpyrrolidine can also be used. Polyethylene glycol, hydrophilic polymers, ethylcellulose and waxes can also serve as binders. A lubricant is necessary in a tablet formulation to prevent the tablet and punches from sticking in the die. The lubricant is chosen from such slippery solids as talc, magnesium and calcium stearate, stearic acid and hydrogenated vegetable oils.

Extended release tablets containing wax materials are generally prepared using methods known in the art such as a direct blend method, a congealing method, and an aqueous dispersion method. In a congealing method, the drug is mixed with a wax material and either spray-congealed or congealed and screened and processed.

Ondansetron extended release tablet of the present invention release ondansetron over up to 14 hours, more preferably up to 12 hours. Tablet can be optionally coated with a layer comprising ondansetron to provide an immediate release (burst) upon administration. In the latter case, immediate ondansetron release is then followed by its slow or extended release over up to 14 hours.

7.4 Separating Layers

A separating layer (seal coat) between the drug-containing core and the delayed release layer is an optional feature of the formulation. The functions of the separating layer, if required, are to provide a smooth base for the application of the delayed release layer, to prolong the core's resistance to acid and/or neutral conditions, and to improve stability by inhibiting any interaction between the drug and the delayed release polymer. In general, the seal coat may be used to separate any two layer of a multi-layer tablet.

The smoothing function of the separating layer is purely mechanical, the objective of which is to improve the coverage of the delayed release layer and to avoid thin spots in it, caused by bumps and irregularities on the core. Accordingly, the more smooth and free of irregularities the core can be made, the less material is needed in the separating layer, and the need for the smoothing characteristic of the separating layer may be avoided entirely when the drug is of extremely fine particle size and the core is made as close as possible to truly spherical.

The inhibition of any tablet core/delayed release layer interaction is mechanical. The separating layer (seal coat) physically keeps the components in the core and polymer layers from coming into direct contact with each other. In some cases, the separating layer can also act as a diffusional barrier to migrating core or polymer layer components dissolved in product moisture. The separating layer can also be used as a light barrier by opacifying it with agents such as titanium dioxide, iron oxides and the like.

In general, the separating layer is composed of coherent or polymeric materials, and finely powdered solid excipients which constitute fillers. When a reduced sugar is used in the separating layer, it is applied in the form of an aqueous solution and constitutes part of or the whole of the coherent material which sticks the separating layer together. In addition to or instead of the reduced sugar, a polymeric material may also be used in the separating layer. For example, substances such as hydroxypropylmethylcellulose, polyvinylpyrrolidone, hydroxypropylcellulose and the like may be used in small amounts to increase the adherence and coherence of the separating layer.

It is further advisable to use a filler excipient in the separating layer to increase the smoothness and solidity of the layer. Substances such as finely powdered talc, silicon dioxide and the like are universally accepted as pharmaceutical excipients and may be added as is convenient in the circumstances to fill and smooth the separating layer.

In general, the amount of sugar in the separating layer may be in the range of from about 2% to about 10% of the product, when a sugar is used at all, and the amount of polymeric or other sticky material may be in the range of from about 0.1 to about 5%. The amount of filler, such as talc, should be in the range of from about 5 to about 15%, based on final product weight.

8. Kit Containing Pharmaceutical Compositions

A kit is provided wherein the pharmaceutical composition of the invention is packaged accompanied by instructions. The packaging material may be a box, bottle, blister package, tray, or card. The kit will include a package insert instructing the patient to take a specific dose at a specific time, for example, a first dose on day one, a second higher dose on day two, a third higher dose on day three, and so on, until a maintenance dose is reached. A preferred kit comprises an ondansetron plus fluoxetine composition with dosage instructions.

9. Methods of Manufacturing

As will be appreciated by those skilled in the art and as described in the pertinent texts and literature, a number of methods are available for preparing drug-containing tablets, beads, granules or particles that provide a variety of drug release profiles. Such methods include, but are not limited to, the following: coating a drug or drug-containing composition with an appropriate coating material, typically although not necessarily, incorporating a polymeric material, increasing drug particle size, placing the drug within a matrix, and forming complexes of the drug with a suitable complexing agent.

The delayed release dosage units may be coated with the delayed release polymer coating using conventional techniques, e.g., using a conventional coating pan, an airless spray technique, fluidized bed coating equipment (with or without a Wurster insert), or the like. For detailed information concerning materials, equipment and processes for preparing tablets and delayed release dosage forms, see Pharmaceutical Dosage Forms: Tablets, eds. Lieberman et al. (New York: Marcel Dekker, Inc., 1989), and Ansel et al., Pharmaceutical Dosage Forms and Drug Delivery Systems, 6.sup.th Ed. (Media, Pa.: Williams & Wilkins, 1995).

A preferred method for preparing extended release tablets is compressing a drug-containing blend, e.g., blend of granules, prepared using a direct blend, wet-granulation, or dry-granulation process. Extended release tablets may also be molded rather than compressed, starting with a moist material containing a suitable water-soluble lubricant. However, tablets are preferably manufactured using compression rather than molding. A preferred method for forming extended release drug-containing blend is to mix drug particles directly with one or more excipients such as diluents (or fillers), binders, disintegrants, lubricants, glidants, and colorants. As an alternative to direct blending, a drug-containing blend may be prepared by using wet-granulation or dry-granulation processes. Beads containing the active agent may also be prepared by any one of a number of conventional techniques, typically starting from a fluid dispersion. For example, a typical method for preparing drug-containing beads involves dispersing or dissolving the active agent in a coating suspension or solution containing pharmaceutical excipients such as polyvinylpyrrolidone, methylcellulose, talc, metallic stearates, silicone dioxide, plasticizers or the like. The admixture is used to coat a bead core such as a sugar sphere (or so-called "non-pareil") having a size of approximately 60 to 20 mesh.

An alternative procedure for preparing drug beads is by blending drug with one or more pharmaceutically acceptable excipients, such as microcrystalline cellulose, lactose, cellulose, polyvinyl pyrrolidone, talc, magnesium stearate, a disintegrant, etc., extruding the blend, spheronizing the extrudate, drying and optionally coating to form the immediate release beads.

All publications cited are incorporated by reference.

10. Administration of Formulations for Treatment of Breathing Disorders

The formulation can be administered to any patient in need thereof. Although preferred patients are human, typically any mammal including domestic animals such as dogs, cats and horses, may also be treated.

The amount of the active ingredients to be administered is chosen based on the amount which provides the desired dose to the patient in need of such treatment to alleviate symptoms or treat a condition.

EXAMPLES

The present invention will be further understood by reference to the following non-limiting examples. It is understood that although the ondansetron—fluoxetine combination is described in the Examples below, various pharmaceutical compositions comprising a serotonin receptor antagonist and a member selected from the group consisting of a serotonin receptor agonist, an SSRI, and an SNRI can be constructed using general principals and specific details of described formulations.

Example 1

Immediate Release Ondansetron Tablet

Ondansetron HCl dihydrate USP from Symed Labs Ltd (India) was used to manufacture immediate release (IR) ondansetron tablet. Ondansetron HCl dihydrate had the following particle size distribution as determined using Malvern Mastersizer 2000: 10% particles below 2.5 microns, 50% particles below 11.7 microns, and 90% particles below 25.2 microns. All % particles are measured in % volume.

The first step of tablet manufacturing process was sifting Ondansetron HCl, Lactose, Prosolv 50, Ac-Di-Sol, and SDS through 40 mesh sieve (400 μm). The second step consisted of dry mixing of sifted material in V-cone blender for 20 minutes. Aerosil and Mg stearate sifted through 40 mesh sieve were then added and the resultant blend further mixed for 10 minutes. The final blend was compressed into tablets with average tablet weight of 75 mg using 4.76 mm round standard concave punch at a hardness of 10-12 Kp.

Batch size was 12,000 tablets and each tablet contained Ondansetron HCl dihydrate equivalent to 8 mg Ondansetron base. Tablet composition of Lot#1 is given below.

| Tablet composition of Lot# 1 | | |
| --- | --- | --- |
| o. Ingredient | Source | Amount per tablet |
| Ondansetron HCl dihydrate USP | Symed Labs | 9.98 mg |
| Lactose (Pharmatose DCL 14) | DMV | 29.14 mg |
| Prosolv 50 | JRS Pharma | 29.14 mg |
| Ac-Di-Sol (5%) | FMC | 3.75 mg |
| SDS (2%) | Himedia | 1.5 mg |
| Aerosil (1%) | Degussa | 0.75 mg |
| Mg stearate (1%) | Aceto Corp. | 0.75 mg |
| Tablet weight | | 75 mg |

The obtained tablets were evaluated for tablet weight variation, thickness, friability, and disintegration time. Tablet weight variation analysis was performed as follows. 10 tablets were selected at random and weighed individually. The weight of all the tablets was in the range of 73.7 mg to 75.9 mg. The average weight was 74.8 mg and the relative standard deviation was 1.09%. The thickness of the tablets ranged from 3.70 to 3.80 mm. Tablet friability was found to be 0.1% and the disintegration time in water at 37° C. was 1 minutes 20 seconds.

Dissolution of IR tablet was examined in 900 ml of pH 6.8 phosphate buffer containing 1% (w/w) SDS in USP dissolution apparatus 2 (paddles) at 50 rpm and at 37° C. Surfactant was added in order to facilitate ondansetron dissolution. Dissolution data obtained for three tablets is presented below.

| Incubation | Ondansetron released, % total | | | |
| --- | --- | --- | --- | --- |
| time, hours | Tablet# 1 | Tablet# 2 | Tablet# 3 | Average |
| 1 | 90 | 86 | 83 | 86 |
| 2 | 96 | 95 | 98 | 96 |
| 3 | 102 | 103 | 102 | 102 |

Example 2

Delayed Release Ondansetron Tablet

Lot#1 IR ondansetron tablets were used to manufacture delayed release (DR) ondansetron tablets. IR tablets were coated with Eudragit L100/S100 blend using solvent coating technique. A seal coat was applied prior to Eudragit coat. The composition of a seal coat and Eudragit coat are given below.

| Seal coating solution composition | | |
| --- | --- | --- |
| No. | Ingredient | Amount per batch |
| 1 | Opadry YS-1-7006 clear | 32 g |
| 2 | Isopropyl Alcohol | 486 g |
| 3 | Purified water | 122 g |
| | Total | 640 g |

To prepare a seal coating solution purified water and isopropyl alcohol were mixed then Opadry YS-1 7006 clear was added slowly to the mixture under vortex in order to avoid formation of lumps. The mixture was stirred until a clear solution was formed.

| Eudragit coating solution composition (L/S ratio is 3/1) | | |
| --- | --- | --- |
| No. | Ingredient | Amount per batch |
| 1 | Eudragit L 100 powder | 123.60 g |
| 2 | Eudragit S 100 powder | 41.20 g |
| 3 | Isopropyl Alcohol | 2345.65 g |
| 4 | Purified Water | 137.33 g |
| 5 | Triethyl citrate | 16.48 g |
| 6 | Talc | 82.40 g |
| | Total | 2746.67 g |

To prepare delayed release coating solution Eudragit L100 and Eudragit S100 were added to isopropyl alcohol with stirring followed by addition of purified water. After solution became clear triethyl citrate was added and the resultant mixture was stirred for 30 minutes. Then talc was added and mixture was stirred for 5 minutes. The resultant coating solution was kept stirred throughout the coating process.

IR Ondansetron tablets were coated first with a seal coating solution to achieve 3% weight gain and then with Eudragit solution to achieve 10%, 15%, 20% and 25% weight gains. Coated tablets were cured for 4 hours at 40° C.

Dissolution of DR Ondansetron tablet with 20% weight coating gain (Lot#2) was examined in USP dissolution apparatus 2 (paddles) at 50 rpm and at 37° C. Dissolution media was 0.1N HCl for first two hours followed by pH 6.8 phosphate buffer containing 1% (w/w) SDS. SDS was added in order to facilitate ondansetron dissolution. The data obtained is presented below.

| Time, hours | Dissolution media | Ondansetron released, % total | | | | | | |
| --- | --- | --- | --- | --- | --- | --- | --- | --- |
| | | Tab 1 | Tab 2 | Tab 3 | Tab 4 | Tab 5 | Tab 6 | Average |
| 2 | 0.1N HCl | 0 | 0 | 0 | 0 | 0 | 0 | 0 |
| 3 | pH 6.8 | 6 | 2 | 5 | 10 | 3 | 0 | 4 |
| 4 | pH 6.8 | 42 | 44 | 55 | 83 | 48 | 60 | 55 |
| 5 | pH 6.8 | 86 | 84 | 94 | 101 | 92 | 91 | 91 |
| 6 | pH 6.8 | 100 | 97 | 102 | 101 | 99 | 97 | 99 |
| 7 | pH 6.8 | 100 | 99 | 99 | 100 | 102 | 98 | 100 |

Example 3

Pharmacokinetic Parameters of Delayed Released Ondansetron Tablet (Lot#2) in Healthy Human Volunteers The ondansetron delayed release tablet (20% coating weight gain, Lot#2) described in Example 2 was tested in a single dose cross-over 6-patient pilot bioavailability study under fed conditions against IR ondansetron tablet (Lot#1) described in the Example 1. Each tablet was placed in a hard gelatin capsule prior to administration to a human subject.

The average ondansetron plasma concentration as a function of time after tablet administration is shown in FIG. 1. Average pharmacokinetic parameters were obtained by determining the pharmacokinetic parameters for each individual study subject and subsequently averaging the values obtained. The calculated pharmacokinetic parameters for immediate release ondansetron tablet are as follows: $T_{max}$ is 4±1 hours, $C_{max}$ is 30±9 ng/ml, and AUC (0-24) is 221±54 ng hr/ml. The calculated pharmacokinetic parameters for delayed release ondansetron tablet are as follows: $T_{max}$ is 14±4 hours, $C_{max}$ is 10±6 ng/ml, and AUC (0-24) is 101±67 ng hr/ml.

Example 4

Delayed Release Ondansetron Tablet (Second Version)

An alternative DR ondansetron tablet could be manufactured as described in the Example 2 with Eudragit coat composition being further enriched with Eudragit L100. Preferred Eudragit combination contains 75-100% (w/w) Eudragit L100 and 25-0% Eudragit S100. Specific examples of the polymer blends suitable for the use in this invention are mixtures containing 80% (w/w) Eudragit L100 and 20% (w/w) Eudragit S100; 90% (w/w) Eudragit L100 and 10% (w/w) Eudragit S100; and 95% (w/w) Eudragit L100 and 5% (w/w) Eudragit S100.

Example 5

Delayed Release Ondansetron Tablet (Third Version)

An alternative DR ondansetron tablet could be manufactured as described in the Example 2 with Eudragit coat composition containing either Eudragit L100 or Eudragit L100-55. In this Example the manufacturing process is simplified since only one polymer, either Eudragit L100 or Eudragit L100-55, is used to form delayed release polymer layer.

Example 6

Delayed Release Ondansetron Tablet (Fourth Version)

Ondansetron immediate release tablets were prepared using conventional wet granulation process. Each tablet contained ondansetron HCl dihydrate equivalent to 24 mg of ondansetron. The formulation excipients are microcrystalline cellulose, PVPK30 as binder, and magnesium stearate as lubricant.

Tablets were coated with Eudragit L100/S100 blend to form a delayed release coat. Polymer blend of Eudragit L100 and Eudragit S100 in the L/S ratio equal 30/70 was used. The samples with the various delayed release coating levels (weight gain, w/w) were collected.

Example 7

Pulsatile Release Ondansetron Dosage Form

In this example, a tablet of the form similar to that shown in FIG. 1 is constructed as follows. A delayed release ondansetron tablet described in the Examples 2, 4-6 is further coated with an ondansetron containing layer. Such a tablet when administered to a patient provides for two pulses of ondansetron at the desired absorption sites. The first pulse is released in the stomach and the second pulse is released in the intestines. The first to second pulse ondansetron ratio is in the range from approximately 5/95 to approximately 95/5 (w/w), preferably from approximately 20/80 to approximately 80/20 (w/w), and the most preferably from approximately 30/70 to approximately 70/30 (w/w). Ondansetron total dose is approximately between 1 and 100 mg. In the preferred embodiment ondansetron total dose is between 1 and 24 mg. Optionally, ondansetron multi-layer tablet is further coated with an enteric polymer.

Example 8

Pulsatile Release Ondansetron Dosage Form (Version 2)

In this example, a delayed release ondansetron tablet described in the Examples 2, 4-6 is combined with an immediate release ondansetron tablet described in the Example 1. Such a capsule when administered to a patient provides for two pulses of ondansetron at the desired absorption sites. The first pulse is released in the stomach and the second pulse is released in the intestines. The first to second pulse ondansetron ratio is in the range from approximately 5/95 to approximately 95/5 (w/w), preferably from approximately 20/80 to approximately 80/20 (w/w), and the most preferably from approximately 30/70 to approximately 70/30 (w/w). Ondansetron total dose is approximately between 1 and 100 mg. In the preferred embodiment ondansetron total dose is between 1 and 24 mg.

An immediate release tablet is optionally coated with an enteric release polymer resulting in no drug being released in the acidic enviromnent of the stomach. Alternatively, the capsule is optionally further coated with an enteric polymer resulting in no drug being released in the acidic environment of the stomach.

Example 9

Immediate Release Ondansetron-Fluoxetine Tablet

Ondansetron HCl dihydrate USP from Natco Pharma Ltd (India) was used to manufacture immediate release (IR) ondansetron-fluoxetine tablet. Prior to tablet manufacturing Ondansetron HCl dihydrate was milled to the following particle size: 10% particles below 1.7 microns, 50% particles below 8.6 microns, and 90% particles below 32.2 microns. Fluoxetine HCl from Divis Pharmaceuticals (India) was used as received and had the following particle size distribution: 10% particles below 1.9 microns, 50% particles below 8.4 microns, and 90% particles below 31.9 microns.

The first step of tablet manufacturing process was sifting Ondansetron HCl, Fluoxetine HCl, Lactose, Prosolv 50, Ac-Di-Sol, and SDS through 40 mesh sieve. The second step consisted of dry mixing of sifted material in V-cone blender for 20 minutes. Aerosil and Mg stearate sifted through 40 mesh sieve were then added and the resultant blend further mixed for 10 minutes. The final blend was compressed into tablets with average tablet weight of 75 mg using 4.76 mm round standard concave punch at a hardness of 10-12 Kp.

Batch size was 1,000 tablets and each tablet contained Ondansetron HCl dihydrate equivalent to 8 mg Ondansetron and Fluoxetine HCl equivalent to 10 mg Fluoxetine. Tablet composition of Lot#3 is given below.

| | Tablet composition of Lot# 3 | | |
|---|---|---|---|
| No. | Ingredient | Source | Amount per tablet |
| 1 | Ondansetron HCl dihydrate USP | Natco Pharma | 9.98 mg |
| 2 | Fluoxetine HCl | Divis Parma | 11.18 mg |

-continued

Tablet composition of Lot# 3

| No. | Ingredient | Source | Amount per tablet |
|---|---|---|---|
| 3 | Lactose (Pharmatose DCL 14) | DMV | 23.55 mg |
| 4 | Prosolv 50 | JRS Pharma | 23.55 mg |
| 5 | Ac-Di-Sol | FMC | 3.75 mg |
| 6 | SDS | Himedia | 1.5 mg |
| 7 | Aerosil | Degussa | 0.75 mg |
| 8 | Mg stearate | Aceto Corp. | 0.75 mg |
|  | Tablet weight |  | 75 mg |

Dissolution of IR tablet was examined in 900 ml of pH 6.8 phosphate buffer containing 1% (w/w) SDS in USP dissolution apparatus 2 (paddles) at 50 rpm and 37° C. Surfactant was added in order to facilitate drug dissolution. HPLC method was used to analyze the dissolution samples. Dissolution data obtained for three tablets is presented below.

| Incubation time, hours | Ondansetron released, % total | | | |
|---|---|---|---|---|
| | Tablet# 1 | Tablet# 2 | Tablet# 3 | Average |
| 1 | 86 | 84 | 87 | 86 |
| 2 | 97 | 96 | 93 | 95 |

| Incubation time, hours | Fluoxetine released, % total | | | |
|---|---|---|---|---|
| | Tablet# 1 | Tablet# 2 | Tablet# 3 | Average |
| 1 | 82 | 79 | 83 | 81 |
| 2 | 94 | 95 | 93 | 94 |

The scale-up 12,000-tablet batch of ondansetron-fluoxetine tablet was manufactured (Lot#4). The manufacturing procedure and a tablet composition was the same as for Lot#3. Lot#4 tablets were evaluated for tablet weight variation, thickness, friability, and disintegration time. Tablet weight variation analysis was performed as follows. 10 tablets were selected at random and weighed individually. The weight of all the tablets was in the range of 74.5 mg to 78.1 mg. The average weight was 75.9 mg and the relative standard deviation was 2.63%. The thickness of the tablets ranged from 3.75 to 3.90 mm. Tablet friability was found to be 0.15% and the disintegration time in water at 37° C. was 4 minutes 32 seconds.

Example 10

Delayed Release Ondansetron-Fluoxetine Tablet

Lot#4 IR ondansetron-fluoxetine tablets were used to manufacture delayed release (DR) ondansetron-fluoxetine tablets. IR tablets were coated with Eudragit L100/S100 blend using solvent coating technique. A seal coat was applied prior to Eudragit coat. The composition of a seal coat and Eudragit coat are given below.

Seal coating solution composition

| No. | Ingredient | Amount per batch |
|---|---|---|
| 1 | Opadry YS-1-7006 clear | 32 g |
| 2 | Isopropyl Alcohol | 486 g |
| 3 | Purified water | 122 g |
|  | Total | 640 g |

To prepare a seal coating solution purified water and isopropyl alcohol were mixed then Opadry YS-1 7006 clear was added slowly to the mixture under vortex in order to avoid formation of lumps. The mixture was stirred until a clear solution was formed.

Eudragit coating solution composition (L/S ratio is 1/3)

| No. | Ingredient | Amount per batch |
|---|---|---|
| 1 | Eudragit L 100 powder | 34.33 g |
| 2 | Eudragit S 100 powder | 102.99 g |
| 3 | Isopropyl Alcohol | 1954.70 g |
| 4 | Purified Water | 114.44 g |
| 5 | Triethyl citrate | 13.73 g |
| 6 | Talc | 68.66 g |
|  | Total | 2288.88 g |

To prepare delayed release coating solution Eudragit L100 and Eudragit S100 were added to isopropyl alcohol with stirring followed by addition of purified water. After solution became clear triethyl citrate was added and the resultant mixture was stirred for 30 minutes. Then talc was added and mixture was stirred for 5 minutes. The resultant coating solution was kept stirred throughout the coating process.

IR ondansetron-fluoxetine tablets were coated first with a seal coating solution to achieve 3% weight gain and then with Eudragit solution to achieve 10%, 15%, 20% and 25% weight gains. Coated tablets were cured for 2 hours at 40° C.

Dissolution of DR ondansetron-fluoxetine tablet with 20% weight coating gain (Lot#5) was examined in USP dissolution apparatus 2 (paddles) at 50 rpm and 37° C. Dissolution media was 0.1N HCl for first two hours followed by pH 6.8 phosphate buffer and then by pH 7.0 phosphate buffer containing 1% (w/w) SDS. SDS was added to phosphate buffer in order to facilitate drug dissolution. HPLC method was used to analyze the dissolution samples. The data obtained is presented below.

| Time, hours | Dissolution media | Tab 1 | Tab 2 | Tab 3 | Tab 4 | Tab 5 | Tab 6 | Average |
|---|---|---|---|---|---|---|---|---|
| | | Ondansetron released, % total Lot# 5 | | | | | | |
| 2 | 0.1N HCl | 0 | 0 | 0 | 0 | 0 | 0 | 0 |
| 3 | pH 6.8 | 0 | 0 | 0 | 0 | 0 | 0 | 0 |
| 4 | pH 6.8 | 0 | 0 | 0 | 0 | 0 | 0 | 0 |
| 5 | pH 6.8 | 0 | 0 | 0 | 0 | 0 | 0 | 0 |
| 6 | pH 6.8 | 23 | 30 | 24 | 25 | 2 | 14 | 20 |
| 7 | pH 6.8 | 35 | 38 | 33 | 36 | 16 | 24 | 30 |
| 8 | pH 7.0 | 42 | 46 | 40 | 43 | 33 | 34 | 40 |
| 10 | pH 7.0 | 58 | 72 | 60 | 60 | 52 | 57 | 60 |
| 12 | pH 7.0 | 88 | 97 | 92 | 91 | 81 | 97 | 91 |

-continued

| Time, hours | Dissolution media | Tab 1 | Tab 2 | Tab 3 | Tab 4 | Tab 5 | Tab 6 | Average |
|---|---|---|---|---|---|---|---|---|
| | | \multicolumn{7}{c}{Fluoxetine released, % total Lot# 5} | | | | | | | |
| 2 | 0.1N HCl | 0 | 0 | 0 | 0 | 0 | 0 | 0 |
| 3 | pH 6.8 | 0 | 0 | 0 | 0 | 0 | 0 | 0 |
| 4 | pH 6.8 | 0 | 0 | 0 | 0 | 0 | 0 | 0 |
| 5 | pH 6.8 | 0 | 0 | 0 | 0 | 0 | 0 | 0 |
| 6 | pH 6.8 | 23 | 31 | 24 | 28 | 2 | 13 | 20 |
| 7 | pH 6.8 | 31 | 36 | 31 | 37 | 15 | 20 | 28 |
| 8 | pH 7.0 | 41 | 40 | 36 | 42 | 29 | 27 | 36 |
| 10 | pH 7.0 | 48 | 47 | 50 | 53 | 47 | 46 | 49 |
| 12 | pH 7.0 | 85 | 94 | 90 | 93 | 81 | 97 | 90 |

Example 11

Delayed Release Ondansetron-Fluoxetine Tablet (Version 2)

In this example, an alternative delayed release ondansetron-fluoxetine formulation is constructed as described in the Example 10 with Eudragit coat composition being enriched with Eudragit L100. Preferred Eudragit combination contains 75-95% (w/w) Eudragit L100 and 25-5% Eudragit S100. Specific examples of the polymer blends suitable for the use in this invention are mixtures containing 80% (w/w) Eudragit L100 and 20% (w/w) Eudragit S100; 90% (w/w) Eudragit L100 and 10% (w/w) Eudragit S100; and 95% (w/w) Eudragit L100 and 5% (w/w) Eudragit S100.

Example 12

Delayed Release Ondansetron-Fluoxetine Tablet (Version 3)

In this example, an alternative delayed release ondansetron-fluoxetine formulation is constructed as described in the Example 10 with Eudragit coat composition containing either Eudragit L100 or Eudragit L100-55. In this Example the manufacturing process is simplified since only one polymer, either Eudragit L100 or Eudragit L100-55, is used to form delayed release polymer layer.

Example 13

A Delayed Release Formulation of Fluoxetine

Fluoxetine quickly disintegrating tablets were prepared using conventional wet granulation process. Each tablet contains 11.17 mg of fluoxetine hydrochloride which is equivalent to 10 mg of fluoxetine. Tablet average weight is 200 mg. The determined physical parameters are as follows: diameter 8 mm, thickness 3.7-3.8 mm, friability less than 0.5%. The formulation excipients are microcrystalline cellulose (87.9% w/w), PVPK30 as binder (2.5% w/w), crosspovidone as super disintegrant (3% w/w), and magnesium stearate as lubricant (1% w/w). Tablet disintegration time is less than one minute in water and in pH 6.8 phosphate buffer.

Tablets were coated first with Opadry® 7006 clear (Colorcon) to form an HPMC seal coat and then with Eudragit L-100/S-100 blend to form a delayed release coat. The weight gain for Opadry® coat was 2% (w/w). Delayed release coating composition containing polymer blend of Eudragit L-100 and Eudragit S-100 in the L/S ratio equal 25/75 was used. The samples with the various delayed release coating levels (weight gain, w/w) were collected.

Example 14

Delayed Release Formulation of Fluoxetine (Version 2)

Fluoxetine immediate release tablets were prepared using conventional wet granulation process. Each tablet contains 11.17 mg of fluoxetine hydrochloride which is equivalent to 10 mg of fluoxetine. Tablet average weight is 80 mg. The formulation excipients are microcrystalline cellulose, PVPK30 as binder, and magnesium stearate as lubricant.

Tablets were coated with Eudragit L100/S100 blend to form a delayed release coat. Polymer blend of Eudragit L100 and Eudragit S100 in the L/S ratio equal 35/65 was used. The samples with the various delayed release coating levels (weight gain, w/w) were collected.

Example 15

Pulsatile Release Ondansetron and Delayed Release Fluoxetine Dosage Form

In this example, a tablet of the form shown in FIG. 1 is constructed as follows. A tablet core comprises ondansetron and fluoxetine combination mixed together with pharmaceutical ingredients commonly used in the art for manufacturing of immediate release dosage forms (see Example 10). Optionally, a tablet core is bi-layer tablet with one layer containing only fluoxetine and another layer containing only ondansetron. Optionally, disintegrates and super disintegrates (used to promote the disruption of the solid mass into smaller particles which are more readily dispersed or dissolved), dispersing or suspending agents (help maintain the dispersion of small particles in a formulation), and dissolution enhancing agents (alter the molecular forces between ingredients to enhance the dissolution of the solute in the solvent) that are commonly used in the art are added to the composition. The tablet core is coated with a delayed release polymer or polymer blend. Preferred polymers include Eudragit L100-55, Eudragit L100, Eudragit S100, and their mixtures wherein Eudragit L100 to Eudragit S100 ratio is from approximately 95/5 to approximately 5/95 (w/w) in order to achieve a second pulse at about 3-8 hours. The preferred Eudragit L100 to Eudragit S100 ratio is from approximately 60/40 to approximately 10/90 (w/w), and the most preferred is from approximately 40/60 to approximately 20/80 (w/w) (see Example 8 and 9). It may be beneficial to use individual polymers such as Eudragit L100-55, Eudragit L100, or Eudragit S100 without blending them together (see Example 10).

The tablet is then further coated with ondansetron layer. Such a tablet is administered to a patient, and provides for two pulses of ondansetron at the desired absorption sites. The first pulse is released in the stomach and the second pulse is released in the small intestine, while the fluoxetine is released at the time of the second pulse of ondansetron. Thus, when such a tablet is taken at bedtime, the therapeutic effect is achieved by two pulses of ondansetron maintaining the optimal plasma level thereof, and one pulse of fluoxetine during the sleeping period, also maintaining optimal levels but without the undesirable effects of fluoxetine administration prior to the beginning of sleep. Optionally, a multi-layer tablet is further coated with an enteric polymer.

The total ondansetron dose is divided between two pulses. The first to second pulse ondansetron ratio is in the range from approximately 50/50 to approximately 95/5 (w/w), preferably from approximately 60/40 to approximately 90/10 (w/w), and the most preferably from approximately 70/30 to approximately 80/20 (w/w).

Ondansetron total dose is approximately between 1 and 100 mg and fluoxetine total dose is approximately between 2 and 60 mg. Ondansetron to fluoxetine ratio is in the range from approximately 10/1 to approximately 1/10 (w/w), preferably from approximately 5/1 to approximately 1/5 (w/w), and the most preferably from approximately 2/1 to approximately 1/2 (w/w).

In the preferred embodiment ondansetron dose is 24 mg and fluoxetine dose is 10 mg. In one preferred embodiment Eudragit L100-55 was used. In another preferred embodiment Eudragit L100 was used.

Alternatively, pulsatile release ondansetron and delayed release fluoxetine dosage form is a capsule depicted in FIG. 4. This dosage form offers the flexibility of second pulse of ondansetron and fluoxetine dose being released at a different time. This can be achieved by coating the tablets with different polymers and/or polymer blends.

Example 16

Pulsatile Release Ondansetron and Immediate Release Fluoxetine Dosage Form

In this example, a tablet of the form shown in FIG. 2 is constructed as follows. A core comprising ondansetron is coated with a delayed release polymer or a blend of polymers and then further coated with ondansetron and fluoxetine. A capsule of the form wherein pulsatile release ondansetron tablet and immediate release fluoxetine tablet are combined in one capsule is shown in FIG. 4. It is understood that composition details described in Example 15 can be applied to this dosage form.

Example 17

Extended Release Ondansetron and Immediate Release Fluoxetine Dosage Form

In this example, a tablet of the invention comprising either extended release ondansetron tablet coated with fluoxetine or a bi-layer tablet wherein one layer is extended release ondansetron and another layer is immediate release fluoxetine is constructed. Optionally, a tri-layer tablet can be formulated wherein the first layer provides immediate release of fluoxetine, the second layer provides immediate release of ondansetron, and the third layer provides extended release of ondansetron. A capsule of the form is shown in FIG. 3. It is understood that composition details described in Example 13 can be applied to this dosage form.

Example 18

Extended Release Ondansetron and Delayed Release Fluoxetine Dosage Form

In this example, a capsule of the form shown in FIG. 3 are prepared. The ondansetron extended release tablet is optionally surrounded by a coating comprising ondansetron. Fluoxetine tablet consists of a core surrounded by a coating of polymers. It is understood that by varying polymer composition used for tablet coating, time of fluoxetine release can be altered. The capsule is optionally further coated with an enteric polymer resulting in no drug being released in the acidic environment of the stomach.

Example 17

Administration to Treat Patients

The formulations of the invention are administered to patients in need thereof. Particularly, the formulation of any of Examples 1-18 are administered to a patient. The patient realizes a diminished incidence or reduced intensity of sleep apnea, or complete cessation of symptoms.

The invention claimed is:

1. A pharmaceutical composition comprising an immediate release dose of ondansetron and a delayed release dose of ondansetron wherein the release of ondansetron from the composition results in a therapeutically effective level of ondansetron in the blood plasma of a subject for a continuous period initiated by a first pulse of ondansetron at from 0 to 2 hours from administration of the composition, followed by a delayed second pulse of ondansetron that extends the period to from 6 to 14 hours from administration of the composition, wherein the ondansetron blood plasma levels have a $C_{max}$ below approximately 400 ng/mL, and wherein the mean blood plasma concentration of ondansetron released from the composition is approximately 20 ng/mL at 14 hours from administration of the composition, approximately 10 ng/mL at 20 hours from administration of the composition, and approximately 8 ng/mL at 24 hours from administration of the composition.

2. A pharmaceutical composition as claimed in claim 1, wherein the continuous period extends to from 7 to 12 hours from administration of the composition.

3. A pharmaceutical composition as claimed in claim 1, wherein the continuous period extends to 8 to 10 hours from administration of the composition.

4. A pharmaceutical composition as claimed in claim 1, which provides a therapeutically effective level of ondansetron over a continuous period initiated at from 15 minutes to 1.5 hours from administration of the composition and extending to between from 7 and to 12 hours from administration of the composition.

5. A pharmaceutical composition as claimed in claim 1, which provides a therapeutically effective level of ondansetron over a continuous period initiated at from 15 minutes to 1.5 hours from administration and extending to from 8 to 10 hours from administration of the composition.

6. A pharmaceutical composition as claimed in claim 1, wherein the antagonist ondansetron is released in more than two pulses.

7. A pharmaceutical composition as claimed in claim 1, wherein the first pulse of ondansetron is released within 30 minutes from administration and the second pulse is released from 1 hour to 4 hours from administration.

8. A pharmaceutical composition as claimed in claim 7, wherein the first pulse of ondansetron is released within 30 minutes of administration and the second pulse is released from 1 to 3 hours from administration.

9. A pharmaceutical composition as claimed in claim 1, further comprising a dose of at least one additional active chosen from selective serotonin reuptake inhibitor ("SSRI"), a serotonin and norepinephrine reuptake inhibitor ("SNRI"), and a serotonin receptor agonist.

10. A pharmaceutical composition as claimed in claim 1, further comprising an SSRI selected from the group consisting of fluoxetine, paroxetine, milnacipran, sertraline, citalopram, escitalopram, and fluvoxamine.

11. A pharmaceutical composition according to claim 10, wherein the SSRI is fluoxetine.

12. A pharmaceutical composition according to claim 1, further comprising at least one other active compound chosen from analgesics, anti-inflammatory drugs, antipyretics, antidepressants, antiepileptics, antihistamines, antimigraine drugs, antimuscarinics, anxiolytics, sedatives, hypnotics, antipsychotics, bronchodilators, anti asthma drugs, cardiovascular drugs, corticosteroids, dopaminergics, electrolytes, gastro-intestinal drugs, muscle relaxants, nutritional agents, vitamins, parasympathomimetics, stimulants, anorectics, and anti-narcoleptics.

13. A pharmaceutical composition according to claim 1, further comprising at least one other active compound chosen from aceclofenac, acetaminophen, almotriptan, alprazolam, amantadine, amcinonide, aminocyclopropane, amitriptyline, amlodipine, amoxapine, amphetamine, aripiprazole, aspirin, atomoxetine, azasetron, azatadine, beclomethasone, benactyzine, benoxaprofen, bermoprofen, betamethasone, bicifadine, bromocriptine, budesonide, buprenorphine, bupropion, buspirone, butorphanol, butriptyline, caffeine, carbamazepine, carbidopa, carisoprodol, celecoxib, chlordiazepoxide, chlorpromazine, choline salicylate, citalopram, clomipramine, clonazepam, clonidine, clonitazene, clorazepate, clotiazepam, cloxazolam, clozapine, codeine, corticosterone, cortisone, cyclobenzaprine, cyproheptadine, demexiptiline, desipramine, desomorphine, dexamethasone, dexanabinol, dextroamphetamine sulfate, dextromoramide, dextropropoxyphene, dezocine, diazepam, dibenzepin, diclofenac sodium, diflunisal, dihydrocodeine, dihydroergotamine, dihydromorphine, dimetacrine, divalproex, tizatriptan, dolasetron, donepezil, dothiepin, doxepin, duloxetine, ergotamine, escitalopram, estazolam, ethosuximide, etodolac, femoxetine, fenamates, fenoprofen, fentanyl, fludiazepam, fluoxetine, fluphenazine, fiurazepam, flurbiprofen, flutazolam, fluvoxamine, frovatriptan, gabapentin, galantamine, gepirone, Ginkgo biloba, granisetron, haloperidol, huperzine A, hydrocodone, hydrocortisone, hydromorphone, hydroxyzine, ibuprofen, imipramine, indiplon, indomethacin, indoprofen, iprindole, ipsapirone, ketanserin, ketoprofen, ketorolac, lesopitron, levodopa, lipase, lofepramine, lorazepam, loxapine, maprotiline, mazindol, mefenamic acid, melatonin, melitracen, memantine, meperidine, meprobamate, mesalamine, metapramine, metaxalone, methadone, methamphetamine, methocarbamol, methyldopa, methylphenidate, methylsalicylate, methysergid(e), metoclopramide, mianserin, mifepristone, minaprine, mirtazapine, moclobemide, modafinil, molindone, morphine, morphine hydrochloride, nabumetone, nadolol, naproxen, naratriptan, nefazodone, neuronatin, nomifensine, nortriptyline, olanzapine, olsalazine, ondansetron, opipramol, orphenadrine, oxaflozane, oxaprozin, oxazepam, oxitriptan, oxycodone, oxymorphone, pancrelipase, parecoxib, paroxetine, pemoline, pentazocine, pepsin, perphenazine, phenacetin, phendimetrazine, phenmetrazine, phenylbutazone, phenytoin, phosphatidylserine, pimozide, pirlindole, piroxicam, pizotifen, pizotyline, pramipexole, prednisolone, prednisone, pregabalin, propranolol, propizepine, propoxyphene, protriptyline, quazepam, quinupramine, reboxetine, reserpine, risperidone, ritanserin, rivastigmine, rizatriptan, rofecoxib, ropinirole, rotigotine, salsalate, sertraline, sibutramine, sildenafil, sulfasalazine, sulindac, sumatriptan, tacrine, temazepam, tetrabenazine, thiazides, thioridazine, thiothixene, tiapride, tiospirone, tizanidine, tofenacin, tolmetin, toloxatone, topiramate, tramadol, trazodone, triazolam, trifluoperazine, trimethobenzamide, trimipramine, tropisetron, valdecoxib, valproic acid, venlafaxine, viloxazine, vitamin E, zimeldine, ziprasidone, zolmitriptan, Zolpidem, zopiclone and isomers, salts, and combinations thereof.

14. A pharmaceutical composition according to claim 1, wherein the ondansetron is in the form of a therapeutically equivalent dose of an individual ondansetron enantiomer or pharmaceutically acceptable salts thereof.

15. A pharmaceutical composition according to claim 1, wherein the ondansetron is in the form of a therapeutically equivalent dose of a mixture of ondansetron enantiomers or pharmaceutically acceptable salts thereof.

16. A pharmaceutical composition according to claim 1, wherein the ondansetron is in the form of a therapeutically equivalent dose of the active metabolite of ondansetron or pharmaceutically acceptable salts thereof.

17. A pharmaceutical composition according to claim 1, further comprising an enteric coating.

18. A pharmaceutical composition according to claim 1, wherein the administrable ondansetron unit dose is from 1 to 100 mg.

19. A pharmaceutical composition according to claim 18, wherein the administrable ondansetron unit dose is from 4 to 40 mg.

20. A pharmaceutical composition according to claim 1, wherein the ondansetron is present in an amount ranging from 4 to 40 mg and wherein the composition further comprises from 2 to 20 mg fluoxetine.

21. A method of ameliorating a sleep related breathing disorder comprising administering to a patient in need thereof a composition according to claim 1.

22. The method of claim 21, wherein the sleep-related breathing disorder is chosen from obstructive sleep apnea syndrome, apnea of prematurity, congenital central hypoventilation syndrome, obesity hypoventilation syndrome, central sleep apnea syndrome, Cheyne-Stokes respiration, and snoring.

23. A pharmaceutical composition according to claim 9, further comprising at least one other active compound chosen from analgesics, anti-inflammatory drugs, antipyretics, antidepressants, antiepileptics, antihistamines, antimigraine drugs, antimuscarinics, anxiolytics, sedatives, hypnotics, antipsychotics, bronchodilators, anti asthma drugs, cardiovascular drugs, corticosteroids, dopaminergics, electrolytes, gastro-intestinal drugs, muscle relaxants, nutritional agents, vitamins, parasympathomimetics, stimulants, anorectics, and anti-narcoleptics.

24. A pharmaceutical composition according to claim 9, wherein the ondansetron is in the form of a therapeutically equivalent dose of an individual ondansetron enantiomer or pharmaceutically acceptable salts thereof.

25. A pharmaceutical composition according to claim 9, wherein the ondansetron is in the form of a therapeutically equivalent dose of a mixture of ondansetron enantiomers or pharmaceutically acceptable salts thereof.

26. A pharmaceutical composition according to claim 9, wherein the ondansetron is in the form of a therapeutically equivalent dose of the active metabolite of ondansetron or pharmaceutically acceptable salts thereof.

27. A pharmaceutical composition according to claim 9, further comprising an enteric coating.

28. A pharmaceutical composition according to claim 9, wherein the administrable ondansetron unit dose is from 1 to 100 mg.

29. A pharmaceutical composition according to claim 28, wherein the administrable ondansetron unit dose is from 4 to 40 mg.

30. A method of ameliorating a sleep-related breathing disorder comprising administering to a patient in need thereof a composition according to claim 1.

31. The method of claim 30, wherein the sleep-related breathing disorder is chosen from obstructive sleep apnea syndrome, apnea of prematurity, congenital central hypoventilation syndrome, obesity hypoventilation syndrome, central sleep apnea syndrome, Cheyne-Stokes respiration, and snoring.

* * * * *